United States Patent
Zanella et al.

(10) Patent No.: US 10,765,621 B2
(45) Date of Patent: Sep. 8, 2020

(54) EXTRACTS OF HALIMIONE PORTULACOIDES AND THEIR APPLICATION

(71) Applicant: Cutech Srl, Padua (IT)

(72) Inventors: Lorenzo Zanella, Venedig-Mestre (IT); Paolo Pertile, San Pietro Viminario (IT)

(73) Assignee: Symrise AG, Holzminden (DE)

( * ) Notice: Subject to any disclaimer, the term of this patent is extended or adjusted under 35 U.S.C. 154(b) by 754 days.

(21) Appl. No.: 15/023,157

(22) PCT Filed: Sep. 16, 2014

(86) PCT No.: PCT/EP2014/069669
§ 371 (c)(1),
(2) Date: Mar. 18, 2016

(87) PCT Pub. No.: WO2015/040010
PCT Pub. Date: Mar. 26, 2015

(65) Prior Publication Data
US 2016/0228351 A1    Aug. 11, 2016

(30) Foreign Application Priority Data
Sep. 22, 2013 (EP) .................................. 13185470

(51) Int. Cl.
*A61K 36/21* (2006.01)
*A61K 36/00* (2006.01)
*A61K 8/97* (2017.01)
*A61Q 7/00* (2006.01)
*A61Q 19/08* (2006.01)
*A61Q 19/04* (2006.01)

(52) U.S. Cl.
CPC ............... *A61K 8/97* (2013.01); *A61K 36/21* (2013.01); *A61Q 7/00* (2013.01); *A61Q 19/04* (2013.01); *A61Q 19/08* (2013.01); *A61K 2236/00* (2013.01); *A61K 2800/805* (2013.01)

(58) Field of Classification Search
None
See application file for complete search history.

(56) References Cited

U.S. PATENT DOCUMENTS

2004/0126352 A1* 7/2004 Jones ....................... A61K 8/97
424/74
2007/0292537 A1 12/2007 Jones et al.

FOREIGN PATENT DOCUMENTS

WO    2012/002950 A1    1/2012

OTHER PUBLICATIONS

Sousa et al, "Heavy metal accumulation in Halimione portulacoides: Intra- and extra-cellular metal binding sites," Chemophere vol. 70, No. 5, Nov. 24, 2007, pp. 850-857.

* cited by examiner

*Primary Examiner* — Michael Barker
*Assistant Examiner* — Randall Winston
(74) *Attorney, Agent, or Firm* — Dilworth & Barrese, LLP

(57) ABSTRACT

New extracts are suggested of *Halimione portulacoides* or sea purslane, and related species of *Halimione*, obtainable by treating the said plant with a solvent selected from the group consisting of $C_1$-$C_4$ aliphatic alcohols, ethyl acetate, water or their mixtures, removing the dissolved extracts from the residues and recovering the pure extracts from the solvent. The extracts show excellent properties particularly in modulating the metabolism of human skin and hair follicles.

7 Claims, No Drawings

EXTRACTS OF HALIMIONE PORTULACOIDES AND THEIR APPLICATION

FIELD OF INVENTION

The present invention relates to the area of cosmetics and toiletries and refers to extracts of the halophyte *Halimione portulacoides* (=*Atriplex portulacoides*), processes and compositions for obtaining them, and their use in hair and skin care applications.

STATE OF THE ART

Throughout the last decades, the cosmetics and toiletry industry has devoted increasing attention to the identification of natural compounds suitable for use in the preparation of body care products, with a special interest in anti-aging products. Natural organisms, in particular plants and their fruits, represent a relevant source of active compounds feeding a rapidly expanding market sector.

Plants are the main source of natural active compounds, on a quantitative basis, with particular reference to antioxidants, vitamins and micronutrients. Many of these active compounds have been shown to protect the body against aging processes and environmental damages. Different risk factors affecting human health, e.g. skin exposure to UV radiation or excessive production of free radicals due to a wrong lifestyle, can similarly be mitigated by abundant vegetables in the diet. The cosmetics industry has become aware that aging represents a more interesting business opportunity than traditional products formulated for improving the physical appearance. In fact, while the pursuit of beauty involves many people, especially women, the desire to stay young involves everyone and, ultimately, a product that prevents aging is itself also a beauty product. A young body naturally expresses harmony and beauty and the skin is probably the organ that more than any other helps to define age. This concept is radically altering the mission of cosmetics, which in addition to creating products to enhance personal appearance, is increasingly seeking to develop products to preserve a youthful appearance. Today, skin anti-aging products are a key target for all the leader companies in the cosmetics sector.

From a socio-economic point of view, industrialized nations are experiencing a significant rise in the mean age of the population, as an effect of the lower birth rate and longer life expectancy. This epochal event significantly increases the impact of anti-aging products in the nutraceutical and cosmetics market. Treatment of the skin is the main field of application for natural active compounds, also because the appearance of the skin depends on different characteristics: colour, smoothness, thickness of the epidermal stratum corneum, presence of wrinkles or spots, presence of hairs, production of sebum etc. As a consequence, specific and differentiated products can be formulated in order to modulate the tissue processes that affect each of these skin features.

Wrinkles are the more visible symptom of skin aging, and the cosmetics industry has been focusing its efforts on this issue for years. The decrease and structural modification of dermis collagen have been recognized as the main cause of skin wrinkles. Collagen stimulators have been actively screened among synthetic compounds and natural ingredients, including microalgae extracts. Other components of the dermis matrix, however, assume relevance for preserving skin youthfulness. Among these, glycosaminoglycans are essential participants in the composition of the dermis matrix and play a fundamental role, among the other functions, in retaining water. Hyaluronic acids is the main glycosaminoglycan involved in the regulation of skin moisture. As a consequence, cosmetics need active ingredients that enhance the natural production of both collagen and hyaluronic acids in the dermis.

However, the epidermis is also a relevant target for treatments aimed to improve the aesthetic of the skin. The basal layer of epidermis is characterized by the continuous proliferation of keratinocytes. They progressively move toward the upper layers and undergo differentiation processes that turn them into corneocytes. The corneocytes are dead cells that, combined with the extracellular lipid matrix (mainly consisting of ceramides, cholesterol and fatty acids), compose the superficial stratum corneum, i.e. the proteolipidic barrier of the skin. The stratum corneum is continuously generated as result of the differentiation process of the underlying keratinocytes, and is superficially removed through a regular process of desquamation. This continuous production and loss of epidermis cells constitutes the perpetual renewal of the skin. Some relevant problems can arise when the differentiation process of the stratum corneum is abnormally stimulated. Dandruff, for instance, is a very common scalp disorder with significant consequences in terms of aesthetics. Since sebum quality and quantity play an important role in the modulation of stratum corneum renewal, a product that inhibits both stratum corneum formation and sebum production would be strongly appreciated by the cosmetics industry.

Corns and calluses are typical consequences of stratum corneum overproduction. They develop in areas of skin exposed to repeated friction or pressure and cosmetic treatment can be desirable to prevent or reduce these slight blemishes. However, more relevant disorders can occur when the epidermis is affected by pathologies that markedly increase its proliferation, such as eczema, lichen planus, seborrheic keratoses etc. Active ingredients that reduce the differentiation process of keratinocytes would therefore be useful for both cosmetic and therapeutic purposes. Psoriasis, a quite common skin disease originating from immune system disorders, induces an accelerated production of new keratinocytes in well-defined skin areas, which become thick, scaly and itchy (psoriasic plaque). Although psoriasis is still not curable, any treatment that reduces the discomfort and aesthetic impact associated with psoriasic plaques would find important applications. The ideal candidate is a compound or preparation that combines anti-inflammatory activity through the inhibition of epidermal proliferation. So far, the main treatments have been based on corticosteroids, but prolonged use has important contraindications. Topical corticosteroids are classified into groups based on potency. For example, the corticosteroid clobetasol proprionate is ranked as a very potent steroid, while betametasone diproprionate and fluocinolone acetonide can range from potent to moderately potent. The least potent are topical preparations containing hydrocortisone. The administration of corticosteroids can be adopted for treating an acute problem, but is inadvisable in the long term as it can lead to several collateral problems.

Natural extracts with similar effects, although they generally express a less potent activity, may be well tolerated even in treatments that, as in the case of psoriasis, are extended over the whole lifetime of a patient. Therefore, the cosmetics and pharmaceutical industries would be extremely interested to discover natural extracts that have anti-inflammatory properties and, at the same time, inhibit the differentiation processes that turn keratinocytes into corneocytes.

There are other conditions, however, in which thickening of the stratum corneum can be desirable and find cosmetic applications. In fact, the prevention of water loss from skin is of primary importance among the functions of the stratum corneum. An insufficient thickness of the stratum corneum can result in a fragile and irritable condition, also associated with xerosis and intense itching in the most severe cases. A balanced stimulation of keratinocyte differentiation may reinforce the epidermal horny layer, improving skin hydration and favouring health and smoothness of the skin.

Another relevant issue for the cosmetic exploitation of natural extracts is modulation of the skin pigmentation. Compounds that can produce a positive modulation of melanogenesis find interesting cosmetic applications, since many people wish to tan their naturally pale skin colour and increase skin pigmentation without being exposed to solar radiation, which promotes the skin aging. Products that stimulate melanogenesis can also be adopted to prepare the body for exposure to intense solar radiation, reducing the risks of sunburn or erythema. This aspect also assumes relevance for the prevention of important skin pathologies due to solar UV rays, such as skin cancer, which can affect people who have suffered periodic sunburn throughout their life.

Another relevant issue related to stimulators of melanogenesis is the development of a treatment aimed to promote or/and preserve an intense and homogeneous hair colour. Although the melanocyte located in the hair follicle shows important metabolic differences from the skin melanocyte, the discovery of natural modulators of melanogenesis has potential applications in both these organs. The prevention of hair whitening is a very important aim for cosmetics, involving both the beauty and anti-aging sectors. For the above reasons, the cosmetics industry is very interested in acquiring safe and effective skin and hair browning agents and active ingredients obtained from natural sources are especially appreciated.

Treatments related to hair follicle problems, primarily hair loss and pigmentation issues, account for an annual market of more than 10 billion US$ despite a lack of truly effective solutions. Hair loss is the main problem to be solved and the 5-alpha-reductase inhibitors are presently considered the more active agents. 5-alpha-reductase is the key enzyme involved in the transformation of testosterone to dihydrotestosterone (DHT), considered the main steroid compound responsible for hair loss in androgenetic alopecia. The active products, commercially available as Minoxidil (Rogaine), Finasteride (Propecia) and Dutasteride (Avodart), have to be administered under medical supervision and cannot be used to treat pregnant women. They can produce several undesired effects while giving satisfactory responses in a limited proportion of treated subjects. Herbal preparations claiming to induce hair growth are available at a low cost, but their effectiveness is usually very limited. On the other hand, unwanted hair also represents a relevant cosmetic issue, and the discovery of new non-toxic agents inhibiting hair growth would find relevant applications. The discovery of active compounds that can modulate the hair follicle metabolism can therefore be usefully exploited in cosmetics whatever their activity, i.e. if they either stimulate or inhibit hair growth.

However, nowadays, modulation of the lipid metabolism also assumes a primary importance for improving personal appearance. The modern lifestyle, characterized by sedentary work often associated with wrong nutritional behaviour, has widely promoted an excessive accumulation of body fat. Many people suffer from this problem with serious consequences not only on their looks and social relationships, but also on their health and life expectancy. There are few solutions to this apart from rigorous slimming diets, fatiguing exercises, or dangerous and invasive operations of aesthetic surgery. In addition, people of normal weight can also be affected by localised fat deposition in the skin subcutis of particular body regions. Cellulite, for instance, is a typical problem related to this unbalanced fat metabolism, scientifically defined as "lipodystrophy" or "edematousfibrosclerotic panniculopathy". Very few cosmetic treatments are presently available for reducing the subcutaneous fatty layer, also referred as subcutis. The cosmetics industry is very interested in the discovery of effective compounds that can prevent the general accumulation of fat in the body, as well as promote lipolysis in the subcutaneous skin tissue.

However, while fat tissue is usually related with aesthetic problems when its presence is excessive, it can also represent a valuable resource to improve the physical appearance. In fact, a moderate amount of hypodermic fat can confer a desirable roundness or turgidity to some parts of the body. When someone wants to substantially remodel their body, they turn to aesthetic surgery to obtain the redistribution of fat by means of injections or autografting interventions. This allows, for instance, relevant augmentation to be obtained of the volume of breasts or buttocks, but this kind of intervention can also be adopted in order to obtain moderate modification of specific parts of the face, such as lips and cheekbones. The interventions on facial regions can, as an alternative, be performed by administering several microinjections of natural fillers, such as collagen or hyaluronic acid, in order to re-establish the fullness and plumpness typical of young skin. However, the skin problems related with this kind of surgery have to be regarded as typical effects of aging and should preferably be treated by preventing or delaying their occurrence.

In fact, it is presently accepted that depletion of the hypodermic fat tissue, also known as lipoatrophy, plays a relevant role in the aging of the skin. In people with normal metabolism of lipids, aging substantially changes the natural distribution of fat within the body, increasing the perivisceral deposits and inhibiting the metabolism of the hypodermic layers, especially in the face, arms and legs. Of course, a reduction of the hypodermal fat layer (subcutis), substantially contributes to modify the appearance of the skin and produces undesirable changes in the body contours, especially on the face. Although aesthetic surgery offers some drastic solutions to some of these problems, as previously said, most people do not want undergo interventions like these, which are expensive and not devoid of risks, such as unwanted reactions or unsatisfactory results.

The cosmetics industry is therefore strongly interested in the discovery of natural ingredients that can delay the physiological reduction of the hypodermal fat. Cosmetic treatments formulated to stimulate synthesis of the dermis matrix in combination with the subcutis lipogenesis would represent an innovative and effective tool to fight skin aging.

Interestingly, agents suitable for modulating the lipogenic processes can also find application in the treatment of skin affected by over-active sebaceous glands (oily skin). While the hypodermal fat is composed of adipocytes, i.e. cells specialized in the synthesis and storage of lipids, the sebaceous glands are composed of sebocytes, which synthesize lipids aimed to be released on the skin surface. Therefore, while lipid synthesis is the specific activity of both these specialized cells, their biological function is fundamentally different and the related mechanisms of regulation might be completely different. As a consequence, it would not be surprising that an inhibitor of the adipocyte metabolism (i.e. the accumulation of lipids) can also stimulate the sebocyte activity, or vice-versa.

Sebaceous glands secret a natural oil, called sebum, which participates with the sweat to form the hydrolipic film that covers the skin. Sebum cooperates to reduce the skin water loss and modulates the composition and proliferation of the natural skin microflora. Overproduction of sebum, however, gives the skin a shiny and aesthetically undesirable appearance and can promote other slight blemishes, such as comedones. In some cases, more relevant disorders can occur in the presence of excessive sebum, such as acne, a skin disease characterized by an inflammatory process of the hair follicle and annexed sebaceous gland. *Propionibacterium* acne is the infectious agent in acne. It can proliferate in sebum and cause the inflamed pustules (pimples) characteristic of acne. As a consequence the cosmetics industry is strongly interested in acquiring suitable compounds to inhibit sebum production, especially if this activity is combined with anti-inflammatory properties.

The present invention is the result of a major research effort aiming to discover natural ingredients or extracts suitable to offer natural and safe solutions to some of the skin problems mentioned above.

This invention refers to the exploitation of the halophyte *Halimione portulacoides* or sea purslane, belonging to the Chenopodiaceae family, as a source of extracts exploitable for developing products aiming to:
  prevent skin aging;
  improve the wellness of hair and prevent hair loss;
  stimulate skin melanogenesis;
  improve and stimulate the synthesis of the extracellular matrix in the human dermis;
  improve and stimulate collagen synthesis in the human dermis;
  modulate the synthesis of the stratum corneum in the epidermis;
  modulate synthesis and secretion of sebum;
  modulate adipogenesis;
  exert anti-inflammatory activity.

This plant occurs in environments periodically flooded by salt water, e.g. salt marshes. These environments are extremely hostile to colonization by terrestrial plants, which need to develop specific adaptive mechanisms to survive stress factors such as saline soil or flooding. Perhaps for these adaptive mechanisms, *Halimione* has surprisingly developed secondary metabolites that are very active on human cells and tissues. So far, this plant was known only for its edible leaves, which can be eaten raw in salads or gently steamed. The leaves are thick and succulent with a crunchy texture and a natural saltiness.

The traditional use of *Halimione* as a food is consistent with the absence of toxicity of the extracts, however, the beneficial effects on cell and tissues revealed with the present invention are completely novel.

Some Chenopodiaceae plants and their extracts have been used to prepare cosmetic and body care products. For instance, JP 63192705 A (Shiseido Co. Ltd) describes preparations from several plants, among which Chenopodiaceae, for improving the smoothness and hydration of the skin. JP 2010013373 A (Pola Chem Ind. Inc.) refers to preparations obtained from other Chenopodiaceae, e.g. *Salicornia europea*, for modulating the horny layer of skin in order to improve the skin barrier functions. Similarly, JP 2005145878 A (Kyoei Chemical Ind. & Kyoei Kagaku Kogyo KK) reveals skin barrier function restorative/antioxidant/anti-inflammatory properties for extracts obtainable from herbs of the genus *Salicornia*.

According to JP 2004331530 A, the Chenopodiaceae *Spinacia oleracea*, has properties useful for improving the skin smoothness and preventing aging. JP 11106318 A (Shiseido Co. Ltd) proposes extracts from Chenopodiaceae of the genus *Chenopodium* or *Poterium* for dandruff repressive treatments of the scalp.

Harunire Kikaku K K & Imai Sumio (JP 3994226 B2) patented extracts obtained from the ripe fruit of the Chenopodiaceae *Kochia scoparia* exhibiting therapeutic or lenitive effects on atopic dermatitis, skin itchiness and eczema.

Therefore, biological properties useful for cosmetics have been demonstrated from some plants belonging to the big and heterogeneous Chenopodiaceae family, but, among the cited species, only *Salicornia* is a halophyte occurring in salty environments similar to the ones colonized by *Halimione*. Nevertheless, *Salicornia* is very different from *Halimione* under many points of view, indeed it belongs to the subfamily Salicornioideae, while *Halimione* is included in the Chenopodioideae.

In conclusion, the prior art is completely silent with regard to the biological properties of *Halimione* for cosmetic applications. The objective of the present invention was to develop extracts based on renewable sources, more particularly on *Halimione portulacoides*, wild or cultivated, suitable for modulating and stimulating the metabolism of human skin and hair follicles. In particular, the objective was to develop new extracts for cosmetic and, respectively, dermatological application:
  increase and/or stimulate melanogenesis in human hair and skin;
  increase human hair growth and/or prevent hair loss;
  promote collagen synthesis in the human dermis;
  promote the synthesis of glycosaminoglycans, hyaluronic acid in particular, in the human dermis;
  promote keratinocyte differentiation and modulation of the horny layer in the human epidermis;
  modulate adipocyte metabolism;
  modulate sebocyte metabolism;
  reduce and/or prevent inflammatory processes of the skin.

DESCRIPTION OF THE INVENTION

The object of the present invention are extracts of *Halimione portulacoides* obtainable by treating the epigeal part of the plant, i.e. branches, leaves and fruits, with a solvent selected from the group consisting of $C_1$-$C_4$ aliphatic alcohols, ethyl acetate, water or their mixtures, removing the dissolved extracts from the residues and recovering the pure extracts from the solvent.

Surprisingly, it was observed that the above extracts exhibit superior properties when compared with products obtained from the market with respect to the desired modulation of human skin and hair follicles, in particular with respect to melanogenesis, hair follicle growth or, alternatively, collagen and hyaluronic acid synthesis, keratinocyte differentiation, metabolism of lipids in adipocytes and sebocytes and, finally, the prevention/inhibition of inflammatory processes. The invention encompasses the observation that the performance of the extracts is strictly linked to the nature of the extractant. In other words, different solvents result in extracts with different compositions and different properties.

Extraction Process

Another object of the present invention relates to a process for obtaining extracts of *Halimione portulacoides* comprising the following steps:

finely mincing parts of the freshly harvested plant using electromechanical devices, blades suitable for manual use or any other method, homogenizing this minced material by pounding it in a mortar together with an extraction solvent selected from the group consisting of $C_1$-$C_4$ aliphatic alcohols, ethyl acetate, water or their mixtures in an amount suitable for the active compounds to move into the solvent phase, optionally at elevated temperatures, removing the dissolved extract from the residue, and recovering the pure extract from the solvent.

Basically, the extracts according to the present invention may be prepared by methods known per se, for example, by aqueous, organic or aqueous/organic extraction of the plants using the above solvents. Suitable extraction processes are any conventional extraction process such as maceration, re-maceration, digestion, agitation maceration, vortex extraction, ultrasonic extraction, counter current extraction, percolation, re-percolation, evacolation (extraction under reduced pressure), diacolation and solid/liquid extraction under continuous reflux. Percolation is advantageous for industrial uses. Any size reduction methods known to the expert may be used, for example, freeze grinding. Preferred solvents for the extraction process are methanol, ethanol, isopropyl alcohol, ethyl acetate and water (preferably water at a temperature above 80° C., and more particularly above 95° C.) or mixtures of these organic solvents and water, more particularly, low molecular weight alcohols with more or less high water contents. An extraction with methanol, ethanol and water-containing mixtures is particularly preferred. The extraction process is generally carried out at temperatures of from about 20 to about 100° C., and preferably from about 50 to about 70° C. In one preferred method, the extraction process is conducted in an inert gas atmosphere to avoid the oxidation of the ingredients of the extract. This is particularly important where extraction is done at temperatures above 40° C. The extraction times are selected by the expert depending on the starting material, extraction process, extraction temperature, and ratio of solvent to raw material, etc. After the extraction process, the crude extracts obtained may optionally be subjected to other typical steps, such as purification, concentration and/or decolouration. If desired, the extracts thus prepared may be subjected, for example, to the selective removal of individual unwanted ingredients. The extraction process may be carried out to any degree, but is usually continued to exhaustion. Typical yields (=extracted dry matter based on the quantity of raw fresh material used) in the extraction of the starting materials are in the order of about 1 to about 20%, preferably from about 1 to about 10%, and more preferably from about 2 to about 6% b.w.—calculated on the starting materials. The extraction is preferably performed on freshly harvested plants, but frozen or lyophilized material may also be used.

In the following, the process for obtaining the extracts according to the invention is described in more detail:

Methanol or Ethanol or Isopropyl Alcohol or Ethyl Acetate Extraction Process: Single Solvent Extraction (a) Each gram of fresh minced and macerated plant was extracted by treatment with 4 ml of solvent, stirring the suspension at room temperature for 16 hours in the dark;

(b) the residual material was separated from the extract by centrifugation at 2000 G for 15 minutes;

(c) the residual material was washed by suspending it in 0.5 ml of solvent;

(d) the cell material was separated from the washing solvent by centrifugation at 2000 G for 15 minutes;

(e) the residual biomass was washed again by suspending it in 0.5 ml of solvent;

(f) the cell material was separated from the washing solvent by centrifugation at 2000 G for 15 minutes;

(g) the firstly collected extract and washing solvent volumes were mixed obtaining the final extract, (h) a sample of extract was evaporated from the solvent in order to weigh the dry residue and estimate its concentration.

Industrial Application

Another object of the present invention is directed at cosmetic compositions comprising extracts of *Halimione portulacoides* and a cosmetically acceptable carrier selected from the group consisting of $C_1$-$C_4$ aliphatic alcohols, polyols having 3 to 12 carbon atoms, oil components, water and their mixtures. Suitable carriers encompass, for example, ethanol, propanol, isopropyl alcohol, all isomeric forms of butanol, ethylene and/or propylene glycol and its dimers and trimers, glycerol, glucose, pentaerythritol and the like. Suitable oil components are disclosed in the following chapter.

The compositions may contain the extracts in amounts of from about 0.001 to about 35% b.w., preferably from about 0.5 to about 20% b.w., more preferably from about 1 to about 10% b.w. and mot preferably from about 2 to about 5% b.w—the amounts calculated on the dry matter of the extracts. The remaining parts are the carriers. Typically, the administration of the extracts takes place topically; however, it is also possible to use the extracts—especially after encapsulation—for oral uptake.

Further objects of the present invention are related to non-pharmaceutical methods for making hair and/or skin care compositions by adding extracts of *Halimione* sp. to a cosmetic base;

for improving sebum production by topical administration of extracts of *Halimione* sp. to human hair or skin;

for modulating growth of human hair by topical administration of extracts of *Halimione* sp. to the scalp.

for preventing and combatting hair loss by topical administration of extracts of *Halimione* sp. to the scalp;

for preventing and combatting skin aging by topical administration of extracts of *Halimione* sp. to the skin;

for improving and stimulating collagen synthesis in the human dermis by topical administration of extracts of *Halimione* sp. to the skin;

for improving and stimulating glucosaminoglycans synthesis by topical administration of extracts of *Halimione* sp. to the skin;

for modulating keratinocyte differentiation in the human epidermis by topical administration of extracts of *Halimione* sp. to the skin or the scalp;

for modulating of the horny layer in the human epidermis by topical administration of *Halimione* sp. extracts of to the skin or the scalp; and for modulating the adipocyte metabolism by topical administration of extracts of *Halimione* sp. to the skin or the scalp.

Cosmetic or Pharmaceutical Compositions

The preparations according to the invention may contain abrasives, anti-acne agents, agents against ageing of the skin, anti-cellulitis agents, antidandruff agents, anti-inflammatory agents, irritation-preventing agents, irritation-inhibiting agents, antioxidants, astringents, perspiration-inhibiting agents, antiseptic agents, ant-statics, binders, buffers, carrier materials, chelating agents, cell stimulants, cleansing agents, care agents, depilatory agents, surface-active substances, deodorizing agents, antiperspirants, softeners, emulsifiers, enzymes, essential oils, fibres, film-forming agents, fixatives, foam-forming agents, foam stabilizers, substances for preventing foaming, foam boosters, gelling agents, gel-forming agents, hair care agents, hair-setting agents, hair-straightening agents, moisture-donating agents, moisturizing substances, moisture-retaining substances, bleaching agents, strengthening agents, stain-removing agents, optically brightening agents, impregnating agents, dirt-repellent agents, friction-reducing agents, lubricants, moisturizing creams, ointments, opacifying agents, plasticizing agents, covering agents, polish, gloss agents, polymers, powders, proteins, re-oiling agents, abrading agents, silicones, skin-soothing agents, skin-cleansing agents, skin care agents, skin-healing agents, skin-lightening agents, skin-protecting agents, skin-softening agents, hair promotion agents, cooling agents, skin-cooling agents, warming agents, skin-warming agents, stabilizers, UV-absorbing agents, UV filters, detergents, fabric conditioning agents, suspending agents, skin-tanning agents, thickeners, vitamins, oils, waxes, fats, phospholipids, saturated fatty acids, mono- or polyunsaturated fatty acids, α-hydroxy acids, polyhydroxyfatty acids, liquefiers, dyestuffs, colour-protecting agents, pigments, anti-corrosives, aromas, flavouring substances, odoriferous substances, polyols, surfactants, electrolytes, organic solvents or silicone derivatives and the like as additional auxiliaries and additives.

Surfactants

Other preferred auxiliaries and additives are anionic and/or amphoteric or zwitterionic surfactants. Typical examples of anionic surfactants are soaps, alkyl benzene-sulfonates, alkanesulfonates, olefin sulfonates, alkylether sulfonates, glycerol ether sulfonates, methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside and Mineralöladditive (Catalysts, Surfactants and Mineral Oil Additives)", Thieme Verlag, Stuttgart, 1978, pages 123-217. The percentage content of surfactants in the preparations may be from 0.1 to 10% by weight and is preferably from 0.5 to 5% by weight, based on the preparation.

Oil Bodies

Suitable oil bodies, which form constituents of the O/W emulsions, are, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxy carboxylic acids with linear or branched $C_6$-$C_{22}$-fatty alcohols, in particular Dioctyl Malate, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, Dicaprylyl Carbonate (Cetiol® CC), Guerbet carbonates, based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicone methicone grades, etc.) and/or aliphatic or naphthenic hydrocarbons, such as, for example, squalane, squalene or dialkylcyclohexanes.

Emulsifiers

Other surfactants may also be added to the preparations as emulsifiers, including for example:

products of the addition of 2 to 30 mol ethylene oxide and/or 0 to 5 mol propylene oxide onto linear $C_{8-22}$ fatty alcohols, onto $C_{12-22}$ fatty acids and onto alkyl phenols containing 8 to 15 carbon atoms in the alkyl group;

$C_{12/18}$ fatty acid monoesters and diesters of addition products of 1 to 30 mol ethylene oxide onto glycerol;

glycerol mono- and diesters and sorbitan mono- and diesters of saturated and unsaturated fatty acids containing 6 to 22 carbon atoms and ethylene oxide addition products thereof;

addition products of 15 to 60 mol ethylene oxide onto castor oil and/or hydrogenated castor oil;

polyol esters and, in particular, polyglycerol esters such as, for example, polyglycerol polyricinoleate, polyglycerol poly-12-hydroxystearate or polyglycerol dimerate isostearate. Mixtures of compounds from several of these classes are also suitable;

addition products of 2 to 15 mol ethylene oxide onto castor oil and/or hydrogenated castor oil;

partial esters based on linear, branched, unsaturated or saturated $C_{6/22}$ fatty acids, ricinoleic acid and 12-hydroxystearic acid and glycerol, polyglycerol, pentaerythritol, -dipentaerythritol, sugar alcohols (for example sorbitol), alkyl glucosides (for example methyl glucoside, butyl glucoside, lauryl glucoside) and polyglucosides (for example cellulose);

mono-, di and trialkyl phosphates and mono-, di- and/or tri-PEG-alkyl phosphates and salts thereof;

wool wax alcohols;

polysiloxane/polyalkyl polyether copolymers and corresponding derivatives;

mixed esters of pentaerythritol, fatty acids, citric acid and fatty alcohol and/or mixed esters of $C_{6-22}$ fatty acids, methyl glucose and polyols, preferably glycerol or polyglycerol, polyalkylene glycols and glycerol carbonate.

The addition products of ethylene oxide and/or propylene oxide onto fatty alcohols, fatty acids, alkylphenols, glycerol mono- and diesters and sorbitan mono- and diesters of fatty acids or onto castor oil are known commercially available products. They are homologue mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as lipid layer enhancers for cosmetic formulations. The preferred emulsifiers are described in more detail as follows:

Partial Glycerides.

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 mol ethylene oxide onto the partial glycerides mentioned are also suitable.

Sorbitan Esters.

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

Polyglycerol Esters.

Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyolesters are the mono-, di- and triesters of trimethylol propane or pentaerythritol with lauric acid, cocofatty acid, tallow fatty acid, palmitic acid, stearic acid, oleic acid, behenic acid and the like optionally reacted with 1 to 30 mol ethylene oxide.

Anionic Emulsifiers.

Typical anionic emulsifiers are aliphatic $C_{12-22}$ fatty acids, such as palmitic acid, stearic acid or behenic acid for example, and $C_{12-22}$ dicarboxylic acids, such as azelaic acid or sebacic acid for example.

Amphoteric Emulsifiers.

Other suitable emulsifiers are amphboteric or zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COON— or —$SO_3H$—group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkyl-aminopropionic acids and alkylaminoacetic acids containing around 8 to 18 carbon atoms in the alkyl group. Particularly preferred ampholytic surfactants are N-cocoalkylamino-propionate, cocoacylaminoethyl amino-propionate and $C_{12/18}$ acyl sarcosine.

Superfatting Agents and Consistency Factors

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystea rates is preferably used.

Thickening Agents and Rheology Additives

Suitable thickeners are polymeric thickeners, such as Aerosil® types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates and electrolytes, such as sodium chloride and ammonium chloride.

Polymers

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, amodimethicone, copolymers of adipic acid and dimethylaminohy-droxypropyl diethylenetriamine (Cartaretine®, Sandoz), copolymers of acrylic acid with dimethyl diallyl ammonium chloride (Merquat® 550, Chemviron), polyaminopolyamides and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar® CBS, Jaguar® C-17, Jaguar® C-16 of Celanese, quaternized ammonium salt polymers such as, for example, Mirapol® A-15, Mirapol® AD-1, Mirapol® AZ-1 of Miranol and the various polyquaternium types (for example 6, 7, 32 or 37) which can be found in the market under the tradenames Rheocare® CC or Ultragel® 300.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacryl-amide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Pearlising Waxes

Suitable pearlising waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxy-substituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Silicones

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in Cosm. Toil. 91, 27 (1976).

Waxes and Stabilizers

Besides natural oils used, waxes may also be present in the preparations, more especially natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes.

Metal salts of fatty acids such as, for example, magnesium, aluminium and/or zinc stearate or ricinoleate may be used as stabilizers.

Primary Sun Protection Factors

Primary sun protection factors in the context of the invention are, for example, organic substances (light filters) which are liquid or crystalline at room temperature and which are capable of absorbing ultraviolet radiation and of releasing the energy absorbed in the form of longer-wave radiation, for example heat.

The formulations according to the invention advantageously contain at least one UV-A filter and/or at least one UV-B filter and/or a broadband filter and/or at least one inorganic pigment. Formulations according to the invention preferably contain at least one UV-B filter or a broadband filter, more particularly preferably at least one UV-A filter and at least one UV-B filter.

Preferred cosmetic compositions, preferably topical formulations according to the present invention comprise one, two, three or more sun protection factors selected from the group consistiung of 4-aminobenzoic acid and derivatives, salicylic acid derivatives, benzophenone derivatives, dibenzoylmethane derivatives, diphenyl acrylates, 3-imidazol-4-yl acrylic acid and esters thereof, benzofuran derivatives, benzylidene malonate derivatives, polymeric UV absorbers containing one or more organosilicon radicals, cinnamic acid derivatives, camphor derivatives, trianilino-s-triazine derivatives, 2-hydroxyphenylbenzotriazole derivatives, phenylbenzimidazole sulfonic acid derivatives and salts thereof, anthranilic acid menthyl esters, benzotriazole derivatives and indole derivatives.

In addition, it is advantageous to combine compounds of formula (I) with active ingredients which penetrate into the skin and protect the skin cells from inside against sunlight-induced damage and reduce the level of cutaneous matrix metalloproteases. Preferred respective ingredients, so called arylhydrocarbon receptor antagonists, are described in WO 2007/128723, incorporated herein by reference. Preferred is 2-benzylidene-5,6-dimethoxy-3,3-dimethylindan-1-one.

The UV filters cited below which can be used within the context of the present invention are preferred but naturally are not limiting.

UV filters which are preferably used are selected from the group consisting of
p-aminobenzoic acid
p-aminobenzoic acid ethyl ester (25 mol) ethoxylated (INCI name: PEG-25 PABA)
p-dimethylaminobenzoic acid-2-ethylhexyl ester
p-aminobenzoic acid ethyl ester (2 mol) N-propoxylated
p-aminobenzoic acid glycerol ester
salicylic acid homomenthyl ester (homosalates) (Neo Heliopan® HMS)
salicylic acid-2-ethylhexyl ester (Neo Heliopan® OS)
triethanolamine salicylate
4-isopropyl benzyl salicylate
anthranilic acid menthyl ester (Neo Heliopan® MA)
diisopropyl cinnamic acid ethyl ester
p-methoxycinnamic acid-2-ethylhexyl ester (Neo Heliopan® AV)
diisopropyl cinnamic acid methyl ester
p-methoxycinnamic acid isoamyl ester (Neo Heliopan® E 1000)
p-methoxycinnamic acid diethanolamine salt
p-methoxycinnamic acid isopropyl ester
2-phenylbenzimidazole sulfonic acid and salts (Neo Heliopan® Hydro)
3-(4'-trimethylammonium) benzylidene bornan-2-one methyl sulfate
beta-imidazole-4(5)-acrylic acid (urocanic acid)
3-(4'-sulfo)benzylidene bornan-2-one and salts
3-(4'-methyl benzylidene)-D,L-camphor (Neo Heliopan® MBC)
3-benzylidene-D,L-camphor
N-[(2 and 4)-[2-(oxoborn-3-ylidene) methyl]benzyl] acrylamide polymer
4,4'-[(6-[4-(1,1-dimethyl)aminocarbonyl) phenylamino]-1,3,5-triazine-2,4-diyl)diimino]-bis-(benzoic acid-2-ethylhexyl ester) (Uvasorb® HEB)
benzylidene malonate polysiloxane (Parsol® SLX)
glyceryl ethylhexanoate dimethoxycinnamate
dipropylene glycol salicylate
tris(2-ethylhexyl)-4,4',4"-(1,3,5-triazine-2,4,6-triyltriimino) tribenzoate (=2,4,6-trianilino-(p-carbo-2'-ethylhexyl-1'-oxy)-1,3,5-triazine) (Uvinul® T150)

Broadband filters which are preferably combined with one or more compounds of formula (I) in a preparation according to the present invention are selected from the group consisting of
2-ethylhexyl-2-cyano-3,3-diphenyl acrylate (Neo Heliopan® 303)
ethyl-2-cyano-3,3'-diphenyl acrylate
2-hydroxy-4-methoxybenzophenone (Neo Heliopan® BB)
2-hydroxy-4-methoxybenzophenone-5-sulfonic acid
dihydroxy-4-methoxybenzophenone
2,4-dihydroxybenzophenone
tetrahydroxybenzophenone
2,2'-dihydroxy-4,4'-dimethoxybenzophenone
2-hydroxy-4-n-octoxybenzophenone
2-hydroxy-4-methoxy-4'-methyl benzophenone
sodium hydroxymethoxybenzophenone sulfonate
disodium-2,2'-dihydroxy-4,4'-dimethoxy-5,5'-disulfobenzophenone
phenol, 2-(2H-benzotriazol-2-yl)-4-methyl-6-(2-methyl-3 (1,3,3,3-tetra methyl-1-(trime-thylsilyl)oxy)disiloxanyl) propyl) (Mexoryl® XL)
2,2'-methylene bis-(6-(2H-benzotriazol-2-yl)-4-1,1,3,3-tetramethylbutyl) phenol) (Tinosorb® M)
2,4-bis-[4-(2-ethylhexyloxy)-2-hydroxyphenyl]-1,3,5-triazine
2,4-bis-[{(4-(2-ethylhexyloxy)-2-hydroxy}phenyl]-6-(4-methoxyphenyl)-1,3,5-triazine (Tinosorb® S)
2,4-bis-[{(4-(3-sulfonato)-2-hydroxypropyloxy)-2-hydroxy}phenyl]-6-(4-methoxyphenyl)-1,3,5-triazine sodium salt
2,4-bis-[{(3-(2-propyloxy)-2-hydroxypropyloxy)-2-hydroxy}phenyl]-6-(4-methoxyphenyl)-1,3,5-triazine
2,4-bis-[{4-(2-ethylhexyloxy)-2-hydroxyl}phenyl]-6-[4-(2-methoxyethyl carbonyl) phenylamino]-1,3,5-triazine
2,4-bis-[{4-(3-(2-propyloxy)-2-hydroxypropyloxy)-2-hydroxyl}phenyl]-6-[4-(2-ethylcarboxyl) phenylamino]-1,3,5-triazine
2,4-bis-[{4-(2-ethylhexyloxy)-2-hydroxyl}phenyl]-6-(1-methylpyrrol-2-yl)-1,3,5-triazine
2,4-bis-[{4-tris-(trimethylsiloxysilylpropyloxy)-2-hydroxyl}phenyl]-6-(4-methoxyphenyl)-1,3,5-triazine
2,4-bis-[{4-(2"-methylpropenyloxy)-2-hydroxyl}phenyl]-6-(4-methoxyphenyl)-1,3,5-triazine
2,4-bis-[{4-(1',1',1',3',5',5',5'-hepta methylsiloxy-2"-methyl-propyloxy)-2-hydroxyl}phenyl]-6-(4-methoxyphenyl)-1,3,5-triazine UV-A filters filters which are preferably combined with one or more compounds of formula (I) in a preparation according to the present invention are selected from the group consisting of
4-isopropyl dibenzoyl methane
terephthalylidene dibornane sulfonic acid and salts (Mexoryl® SX)
4-t-butyl-4'-methoxydibenzoyl methane (avobenzone)/(Neo Heliopan® 357)
phenylene bis-benzimidazyl tetrasulfonic acid disodium salt (Neo Heliopan® AP)
2,2'-(1,4-phenylene)-bis-(1H-benzimidazole-4,6-disulfonic acid), monosodium salt
2-(4-diethylamino-2-hydroxybenzoyl) benzoic acid hexyl ester (Uvinul® A Plus)
indanylidene compounds in accordance with DE 100 55 940 A1 (=WO 2002 038537 A1)

UV filters which are more preferably combined with one or more compounds of formula (I) in a preparation according to the present invention are selected from the group consisting of
p-aminobenzoic acid
3-(4'-trimethylammonium) benzylidene bornan-2-one methyl sulfate
salicylic acid homomenthyl ester (Neo Heliopan® HMS)
2-hydroxy-4-methoxybenzophenone (Neo Heliopan® BB)
2-phenylbenzimidazole sulfonic acid (Neo Heliopan® Hydro)
terephthalylidene dibornane sulfonic acid and salts (Mexoryl® SX)
4-tert-butyl-4'-methoxydibenzoyl methane (Neo Heliopan® 357)
3-(4'-sulfo)benzylidene bornan-2-one and salts
2-ethylhexyl-2-cyano-3,3-diphenyl acrylate (Neo Heliopan® 303)
N-[(2 and 4)-[2-(oxoborn-3-ylidene) methyl]benzyl] acrylamide polymer
p-methoxycinnamic acid-2-ethylhexyl ester (Neo Heliopan® AV)

p-aminobenzoic acid ethyl ester (25 mol) ethoxylated (INCI name: PEG-25 PABA)
p-methoxycinnamic acid isoamyl ester (Neo Heliopan® E1000)
2,4,6-trianilino-(p-carbo-2'-ethylhexyl-1'-oxy)-1,3,5-triazine (Uvinul® T150) phenol,
2-(2H-benzotriazol-2-yl)-4-methyl-6-(2-methyl-3(1,3,3,3-tetramethyl-1-(trimethylsilyl)oxy)disiloxyanyl) propyl) (Mexoryl® XL)
4,4'-[(6-[4-(1,1-dimethyl)aminocarbonyl) phenylamino]-1,3,5-triazine-2,4-diyl)diimino]-bis-(benzoic acid-2-ethylhexyl ester) (Uvasorb HEB)
3-(4'-methyl benzylidene)-D,L-camphor (Neo Heliopan® MBC)
3-benzylidene camphor
salicylic acid-2-ethylhexyl ester (Neo Heliopan® OS)
4-dimethylaminobenzoic acid-2-ethylhexyl ester (Padimate O)
hydroxy-4-methoxybenzophenone-5-sulfonic acid and Na salt
2,2'-methylene bis-(6-(2H-benzotriazol-2-yl)-4-1,1,3,3-tetramethylbutyl) phenol) (Tinosorb® M)
phenylene bis-benzimidazyl tetrasulfonic acid disodium salt (Neo Heliopan® AP)
2,4-bis-[{(4-(2-ethylhexyloxy)-2-hydroxyl}phenyl]-6-(4-methoxyphenyl)-1,3,5-triazine (Tinosorb® S)
benzylidene malonate polysiloxane (Parsol® SLX)
menthyl anthranilate (Neo Heliopan® MA)
2-(4-diethylamino-2-hydroxybenzoyl) benzoic acid hexyl ester (Uvinul® A Plus)
indanylidene compounds in accordance with DE 100 55 940 (=WO 02/38537).

Advantageous primary and also secondary sun protection factors are mentioned in WO 2005 123101 A1. Advantageously, these preparations contain at least one UVA filter and/or at least one UVB filter and/or at least one inorganic pigment. The preparations may be present here in various forms such as are conventionally used for sun protection preparations. Thus, they may be in form of a solution, an emulsion of the water-in-oil type (W/O) or of the oil-in-water type (O/W) or a multiple emulsion, for example of the water-in-oil-in-water type (W/O/W), a gel, a hydrodispersion, a solid stick or else an aerosol.

In a further preferred embodiment a formulation according to the invention contains a total amount of sunscreen agents, i.e. in particular UV filters and/or inorganic pigments (UV filtering pigments) so that the formulation according to the invention has a light protection factor of greater than or equal to 2 (preferably greater than or equal to 5). Such formulations according to the invention are particularly suitable for protecting the skin and hair.

Secondary Sun Protection Factors

Besides the groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example alpha-carotene, beta-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, alpha-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages, also (metal) chelators (for example alpha-hydroxyfatty acids, palmitic acid, phytic acid, lactoferrine), alpha-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, superoxide dismutase, titanium dioxide (for example dispersions in ethanol), zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Advantageous inorganic secondary light protection pigments are finely dispersed metal oxides and metal salts which are also mentioned in WO 2005 123101 A1. The total quantity of inorganic pigments, in particular hydrophobic inorganic micro-pigments in the finished cosmetic preparation according to the present invention is advantageously from 0.1 to 30% by weight, preferably 0.5 to 10.0% by weight, in each case based on the total weight of the preparation.

Also preferred are particulate UV filters or inorganic pigments, which can optionally be hydrophobed, can be used, such as the oxides of titanium ($TiO_2$), zinc (ZnO), iron ($Fe_2O_3$), zirconium ($ZrO_2$), silicon ($SiO_2$), manganese (e.g. MnO), aluminium ($Al_2O_3$), cerium (e.g. $Ce_2O_3$) and/or mixtures thereof.

Actives Modulating Skin and/or Hair Pigmentation

Preferred active ingredients for skin and/or hair lightening are selected from the group consisting of:

Kojic acid (5-hydroxy-2-hydroxymethyl-4-pyranone), kojic acid derivatives, preferably kojic acid dipalmitate, arbutin, ascorbic acid, ascorbic acid derivatives, preferably magnesium ascorbyl phosphate, hydroquinone, hydroquinone derivatives, resorcinol, resorcinol derivatives, preferably 4-alkylresorcinols and 4-(1-phenylethyl)1,3-dihydroxybenzene (phenylethyl resorcinol), cyclohexylcarbamates (preferably one or more cyclohexyl carbamates disclosed in WO 2010/122178 and WO 2010/097480), sulfur-containing molecules, preferably glutathione or cysteine, alpha-hydroxy acids (preferably citric acid, lactic acid, malic acid), salts and esters thereof, N-acetyl tyrosine and derivatives, undecenoyl phenylalanine, gluconic acid, chromone derivatives, preferably aloesin, flavonoids, 1-aminoethyl phosphinic acid, thiourea derivatives, ellagic acid, nicotinamide (niacinamide), zinc salts, preferably zinc chloride or zinc gluconate, thujaplicin and derivatives, triterpenes, preferably maslinic acid, sterols, preferably ergosterol, benzofuranones, preferably senkyunolide, vinyl guiacol, ethyl guiacol, dionic acids, preferably octodecene dionic acid and/or azelaic acid, inhibitors of nitrogen oxide synthesis, preferably L-nitroarginine and derivatives thereof, 2,7-dinitroindazole or thiocitrulline, metal chelators (preferably alpha-hydroxy fatty acids, phytic acid, humic acid, bile acid, bile extracts, EDTA, EGTA and derivatives thereof), retinoids, soy milk and extract, serine protease inhibitors or lipoic acid or other synthetic or natural active ingredients for skin and hair lightening, the latter preferably used in the form of an extract from plants, preferably bearberry extract, rice extract, *papaya* extract, turmeric extract, mulberry extract, bengkoang extract, nutgrass extract, liquorice root extract or constituents concentrated or isolated therefrom, preferably glabridin or licochalcone A, *artocarpus* extract, extract of *rumex* and ramulus species, extracts of pine species (*pinus*), extracts of *vitis* species or stilbene derivatives isolated or concentrated therefrom, saxifrage extract, scutelleria extract, grape extract and/or microalgae extract, in particular *Tetraselmis suecica* Extract.

Preferred skin lighteners as component (b) are kojic acid and phenylethyl resorcinol as tyrosinase inhibitors, beta- and alpha-arbutin, hydroquinone, nicotinamide, dioic acid, Mg ascorbyl phosphate and vitamin C and its derivatives, mulberry extract, Bengkoang extract, *papaya* extract, turmeric extract, nutgrass extract, licorice extract (containing glycyrrhizin), alpha-hydroxy-acids, 4-alkylresorcinols, 4-hydroxyanisole. These skin lighteners are preferred due to their very good activity, in particular in combination with sclareolide according to the present invention. In addition, said preferred skin lighteners are readily available.

Advantageous skin and hair tanning active ingredients in this respect are substrates or substrate analogues of tyrosinase such as L-tyrosine, N-acetyl tyrosine, L-DOPA or L-dihydroxyphenylalanine, xanthine alkaloids such as caffeine, theobromine and theophyl-line and derivatives thereof, proopiomelanocortin peptides such as ACTH, alpha-MSH, peptide analogues thereof and other substances which bind to the melanocortin receptor, peptides such as Val-Gly-Val-Ala-Pro-Gly, Lys-Ile-Gly-Arg-Lys or Leu-Ile-Gly-Lys, purines, pyrimidines, folic acid, copper salts such as copper gluconate, chloride or pyrrolidonate, 1,3,4-oxadi-azole-2-thiols such as 5-pyrazin-2-yl-1,3,4-oxadiazole-2-thiol, curcumin, zinc diglycinate (Zn(Gly)2), manganese(II) bicarbonate complexes ("pseudocat-alases") as described for example in EP 0 584 178, tetrasubstituted cyclohexene deriva-tives as described for example in WO 2005/032501, isoprenoids as described in WO 2005/102252 and in WO 2006/010661, melanin derivatives such as Melasyn-100 and MelanZe, diacyl glycerols, aliphatic or cyclic diols, psoralens, prostaglandins and analogues thereof, activators of adenylate cyclase and compounds which activate the transfer of melanosomes to keratinocytes such as serine proteases or agonists of the PAR-2 receptor, extracts of plants and plant parts of the *chrysanthemum* species, *sanguisorba* species, walnut extracts, urucum extracts, rhubarb extracts, microalgae extracts, in particular *Isochrysis galbana*, trehalose, erythrulose and dihydroxyacetone. Flavonoids which bring about skin and hair tinting or browning (e.g. quercetin, rhamnetin, kaempferol, fisetin, genistein, daidzein, chrysin and apigenin, epicatechin, diosmin and diosmetin, morin, quercitrin, naringenin, hesperidin, phloridzin and phloretin) can also be used.

The amount of the aforementioned examples of additional active ingredients for the modulation of skin and hair pigmentation (one or more compounds) in the products according to the invention is then preferably 0.00001 to 30 wt. %, preferably 0.0001 to 20 wt. %, particularly preferably 0.001 to 5 wt. %, based on the total weight of the preparation.

Anti-Aging Actives

In the context of the invention, anti-ageing or biogenic agents are, for example antioxidants, matrix-metalloproteinase inhibitors (MMPI), skin moisturizing agents, glycosaminglycan stimulkators, anti-inflammatory agents, TRPV1 antagonists and plant extracts.

Antioxidants.

Suitable antioxidants encompass amino acids (preferably glycine, histidine, tyrosine, tryptophane) and derivatives thereof, imidazoles (preferably urocanic acid) and derivatives thereof, peptides, preferably D,L-carnosine, D-carnosine, L-carnosine and derivatives thereof (preferably anserine), carnitine, creatine, matrikine peptides (preferably lysyl-threonyl-threonyl-lysyl-serine) and palmitoylated pentapeptides, carotenoids, carotenes (preferably alpha-carotene, beta-carotene, lycopene) and derivatives thereof, lipoic acid and derivatives thereof (preferably dihydrolipoic acid), aurothioglucose, propyl thiouracil and other thiols (preferably thioredoxine, glutathione, cysteine, cystine, cystamine and glycosyl, N-acetyl, methyl, ethyl, propyl, amyl, butyl and lauryl, palmitoyl, oleyl, gamma-linoleyl, cholesteryl, glyceryl and oligoglyceryl esters thereof) and salts thereof, dilauryl thiodipropionate, distearyl thiodipropionate, thiodipropionic acid and derivatives thereof (preferably esters, ethers, peptides, lipids, nucleotides, nucleosides and salts) and sulfoximine compounds (preferably buthionine sulfoximines, homocysteine sulfoximine, buthionine sulfones, penta-, hexa-, heptathionine sulfoximine) in very small tolerated doses (e.g. pmol to µmol/kg), also (metal) chelators (preferably alpha-hydroxy fatty acids, palmitic acid, phytic acid, lactoferrin, alpha-hydroxy acids (preferably citric acid, lactic acid, malic acid), humic acid, bile acid, bile extracts, tannins, bilirubin, biliverdin, EDTA, EGTA and derivatives thereof), unsaturated fatty acids and derivatives thereof (preferably gamma-linolenic acid, linoleic acid, oleic acid), folic acid and derivatives thereof, ubiquinone and derivatives thereof, ubiquinol and derivatives thereof, vitamin C and derivatives (preferably ascorbyl palmitate, Mg ascorbyl phosphate, ascorbyl acetate, ascorbyl glucoside), tocopherols and derivatives (preferably vitamin E acetate), vitamin A and derivatives (vitamin A palmitate) and coniferyl benzoate of benzoic resin, rutinic acid and derivatives thereof, flavonoids and glycosylated precursors thereof, in particular quercetin and derivatives thereof, preferably alpha-glucosyl rutin, rosmarinic acid, carnosol, carnosolic acid, resveratrol, caffeic acid and derivatives thereof, sinapic acid and derivatives thereof, ferulic acid and derivatives thereof, curcuminoids, chlorogenic acid and derivatives thereof, retinoids, preferably retinyl palmitate, retinol or tretinoin, ursolic acid, levulinic acid, butyl hydroxytoluene, butyl hydroxyanisole, nordihydroguaiac acid, nordihydroguaiaretic acid, trihydroxybutyrophenone, uric acid and derivatives thereof, mannose and derivatives thereof, zinc and derivatives thereof (preferably ZnO, $ZnSO_4$), selenium and derivatives thereof (preferably selenium methionine), superoxide dismutase, stilbenes and derivatives thereof (preferably stilbene oxide, trans-stilbene oxide) and the derivatives (salts, esters, ethers, sugars, nucleotides, nucleosides, peptides and lipids) of these cited active ingredients which are suitable according to the invention or extracts or fractions of plants having an antioxidant effect, preferably green tea, rooibos, honeybush, grape, rosemary, sage, melissa, thyme, lavender, olive, oats, cocoa, ginkgo, *ginseng*, liquorice, honeysuckle, *sophora, pueraria, pinus*, citrus, *Phyllanthus emblica* or St. John's wort, grape seeds, wheat germ, *Phyllanthus emblica*, coenzymes, preferably coenzyme Q10, plastoquinone and menaquinone. Preferred antioxidants are selected from the group consisting of vitamin A and derivatives, vitamin C and derivatives, tocopherol and derivatives, preferably tocopheryl acetate, and ubiquinone.

If vitamin E and/or derivatives thereof are used as the antioxidant(s), it is advantageous to choose their concentrations from the range from about 0.001 to about 10% b.w. based on the total weight of the formulation. If vitamin A or vitamin A derivatives or carotenes or derivatives thereof are used as the antioxidant(s), it is advantageous to choose their concentrations from the range from about 0.001 to about 10% b.w. based on the total weight of the formulation.

Matrix-Metalloproteinase Inhibitors (MMPI).

Preferred compositions comprise matrix-metalloproteinase inhibitors, especially those inhibiting matrix-metalloproteinases enzymatically cleaving collagen, selected from the group consisting of: ursolic acid, retinyl palmitate, propyl gallate, precocenes, 6-hydroxy-7-methoxy-2,2-dimethyl-1 (2H)-benzopyran, 3,4-dihydro-6-hydroxy-7-methoxy-2,2-dimethyl-1(2H)-benzopyran, benzamidine hydrochloride, the cysteine proteinase inhibitors N-ethylmaleimide and epsilon-amino-n-caproic acid of the serinprotease inhibitors: phenylmethylsufonylfluoride, collhibin (company Pentapharm; INCI: hydrolysed rice protein), oenotherol (company Soliance; INCI: propylene glycol, aqua, *Oenothera biennis* root extract, ellagic acid and ellagitannins, for example from pomegranate), phosphoramidone hinokitiol, EDTA, galardin, EquiStat (company Collaborative Group; apple fruit extract, soya seed extract, ursolic acid, soya isoflavones and soya proteins), sage extracts, MDI (company Atrium; INCI: glycosaminoglycans), fermiskin (company Silab/Mawi; INCI: water and lentinus *edodes* extract), actimp 1.9.3 (company Expanscience/Rahn; INCI: hydrolysed lupine protein), lipobelle soyaglycone (company Mibelle; INCI: alcohol, polysorbate 80, lecithin and soy isoflavones), extracts from green and black tea and further plant extracts, which are listed in WO 02 069992 A1 (see tables 1-12 there, incorporated herein by reference), proteins or glycoproteins from soya, hydrolysed proteins from rice, pea or lupine, plant extracts which inhibit MMPs, preferably extracts from shiake mushrooms, extracts from the leaves of the Rosaceae family, sub-family Rosoideae, quite particularly extracts of blackberry leaf (preferably as described in WO 2005 123101 A1, incorporated herein by reference) as e.g. SymMatrix (company Symrise, INCI: Maltodextrin, *Rubus Fruticosus* (Blackberry) Leaf Extract). Preferred actives of are selected from the group consisting of retinyl palmitate, ursolic acid, extracts from the leaves of the Rosaceae family, sub-family Rosoideae, genistein and daidzein.

Skin-Moisturizing Agents.

Preferred skin moisturizing agents are selected from the group consisting of alkane diols or alkane triols comprising 3 to 12 carbon atoms, preferably $C_3$-$C_{10}$-alkane diols and $C_3$-$C_{10}$-alkane triols. More preferably the skin moisturizing agents are selected from the group consisting of: glycerol, 1,2-propylene glycol, 1,2-butylene glycol, 1,3-butylene glycol, 1,2-pentanediol, 1,2-hexanediol, 1,2-octanediol and 1,2-decanediol.

Glycosaminoglycan Stimulators.

Preferred compositions comprise substances stimulating the synthesis of glycosaminoglycans selected from the group consisting of hyaluronic acid and derivatives or salts, Subliskin (Sederma, INCI: *Sinorhizobium Meliloti* Ferment Filtrate, Cetyl Hydroxyethylcellulose, Lecithin), Hyalufix (BASF, INCI: Water, Butylene Glycol, *Alpinia galanga* leaf extract, Xanthan Gum, Caprylic/Capric Triglyceride), Stimulhyal (Soliance, INCI: Calcium ketogluconate), Syn-Glycan (DSM, INCI: Tetradecyl Aminobutyroylvalylaminobutyric Urea Trifluoroacetate, Glycerin, Magnesium chloride), Kalpariane (Biotech Marine), DC Upregulex (Distinctive Cosmetic Ingredients, INCI: Water, Butylene Glycol, Phospholipids, Hydrolyzed Sericin), glucosamine, N-acetyl glucosamine, retinoids, preferably retinol and vitamin A, *Arctium lappa* fruit extract, *Eriobotrya japonica* extract, Genkwanin, N-Methyl-L-serine, (−)-alpha-bisabolol or synthetic alpha-bisabolol such as e.g. Dragosantol and Dragosantol 100 from Symrise, oat glucan, *Echinacea purpurea* extract and soy protein hydrolysate. Preferred actives are selected from the group consisting of hyaluronic acid and derivatives or salts, retinol and derivatives, (−)-alpha-bisabolol or synthetic alpha-bisabolol such as e.g. Dragosantol and Dragosantol 100 from Symrise, oat glucan, *Echinacea purpurea* extract, *Sinorhizobium Meliloti* Ferment Filtrate, Calcium ketogluconate, *Alpinia galanga* leaf extract and tetradecyl aminobutyroylvalylaminobutyric urea trifluoroacetate.

Anti-Inflammatory Agents.

The compositions may also contain anti-inflammatory and/or redness and/or itch ameliorating ingredients, in particular steroidal substances of the corticosteroid type selected from the group consisting of hydrocortisone, dexamethasone, dexamethasone phosphate, methyl prednisolone or cortisone, are advantageously used as anti-inflammatory active ingredients or active ingredients to relieve reddening and itching, the list of which can be extended by the addition of other steroidal anti-inflammatories. Nonsteroidal anti-inflammatories can also be used. Examples which can be cited here are oxicams such as piroxicam or tenoxicam; salicylates such as aspirin, disalcid, solprin or fendosal; acetic acid derivatives such as diclofenac, fenclofenac, indomethacin, sulindac, tolmetin or clindanac; fenamates such as mefenamic, meclofenamic, flufenamic or niflumic; propionic acid derivatives such as ibuprofen, naproxen, benoxaprofen or pyrazoles such as phenylbutazone, oxyphenylbutazone, febrazone or azapropazone. Anthranilic acid derivatives, in particular avenanthramides described in WO 2004 047833 A1, are preferred anti-itch ingredients in a composition according to the present invention.

Also useful are natural or naturally occurring anti-inflammatory mixtures of substances or mixtures of substances that alleviate reddening and/or itching, in particular extracts or fractions from camomile, Aloe vera, *Commiphora* species, *Rubia* species, willow, willow-herb, oats, calendula, *arnica*, St John's wort, honeysuckle, rosemary, *Passiflora incarnata*, witch hazel, ginger or *Echinacea*; preferably selected from the group consisting of extracts or fractions from camomile, Aloe vera, oats, calendula, *arnica*, honeysuckle, rosemary, witch hazel, ginger or *Echinacea*, and/or pure substances, preferably alpha-bisabolol, apigenin, apigenin-7-glucoside, gingerols, shogaols, gingerdiols, dehydrogingerdiones, paradols, natural or naturally occuring avenanthramides, preferably tranilast, avenanthramide A, avenanthramide B, avenanthramide C, non-natural or non-naturally occuring avenanthramides, preferably dihydroavenanthramide D, dihydroavenanthramide E, avenanthramide D, avenan-thramide E, avenanthramide F, boswellic acid, phytosterols, glycyrrhizin, glabridin and licochalcone A; preferably selected from the group consisting of alpha-bisabolol, natural avenanthramides, non-natural avenanthr-amides, preferably dihydroavenanthramide D (as described in WO 2004 047833 A1), boswellic acid, phytosterols, glycyrrhizin, and licochalcone A, and/or allantoin, panthenol, lanolin, (pseudo-)ceramides [preferably Ceramide 2, hydroxypropyl bispalmitamide MEA, cetyloxypropyl glyceryl methoxypropyl myristamide, N-(1-hexadecanoyl)-4-hydroxy-L-proline (1-hexadecyl) ester, hydroxyethyl palmityl oxyhydroxypropyl palmitamide], glycosphingolipids, phytosterols, chitosan, mannose, lactose and β-glucans, in particular 1,3-1,4-β-glucan from oats.

When bisabolol is used in the context of the present invention it can be of natural or synthetic origin, and is preferably "alpha-bisabolol". Preferably, the bisabolol used is synthetically prepared or natural (−)-alpha-bisabolol and/or synthetic mixed-isomer alpha-bisabolol. If natural (−)-alpha-bisabolol is used, this can also be employed as a constituent of an essential oil or of a plant extract or of a fraction thereof, for example as a constituent of (fractions of) oil or extracts of camomile or of *Vanillosmopsis* (in particular *Vanillosmopsis erythropappa* or *Vanillosmopsis arborea*). Synthetic alpha-bisabolol is obtainable, for example, under the name "Dragosantol" from Symrise.

In case ginger extract is used in the context of the present invention, preferably extracts of the fresh or dried ginger root are used which are prepared by extraction with methanol, ethanol, iso-propanol, acetone, ethyl acetate, carbon dioxide (CO2), hexane, methylene chloride, chloroform or other solvents or solvent mixtures of comparable polarity. The extracts are characterized by the presence of active skin irritation-reducing amounts of constituents such as e.g. gingerols, shogaols, gingerdiols, dehydrogingerdiones and/or paradols.

TRPV1 Antagonists.

Suitable compounds which reduce the hypersensitivity of skin nerves based on their action as TRPV1 antagonists, encompass e.g. trans-4-tert-butyl cyclohexanol as described in WO 2009 087242 A1, or indirect modulators of TRPV1 by an activation of the µ-receptor, e.g. acetyl tetrapeptide-15, are preferred.

Desquamating Agents.

The compositions may also contain desquamating agents (component b5) in amounts of about 0.1 to about 30% b.w. preferably about 0.5 to about 15% b.w., particularly preferably about 1 to about 10% b.w. based on the total weight of the preparation. The expression "desquamating agent" is understood to mean any compound capable of acting:

either directly on desquamation by promoting exfoliation, such as β-hydroxy acids, in particular salicylic acid and its derivatives (including 5-n-octanoylsalicylic acid); α-hydroxy acids, such as glycolic, citric, lactic, tartaric, malic or mandelic acids; urea; gentisic acid; oligofucoses; cinnamic acid; extract of *Sophora japonica*; resveratrol and some derivatives of jasmonic acid;

or on the enzymes involved in the desquamation or the degradation of the corneodesmosomes, glycosidases, stratum corneum chymotryptic enzyme (SCCE) or other proteases (trypsin, chymotrypsin-like). There may be mentioned agents chelating inorganic salts: EDTA; N-acyl-N,N',N'-ethylenediaminetriacetic acid; aminosulphonic compounds and in particular (N-2-hydroxyethylpiperazine-N-2-ethane)sulphonic acid (HEPES); derivatives of 2-oxothiazolidine-4-carboxylic acid (procysteine); derivatives of alpha-amino acids of the glycine type (as described in EP-0 852 949, and sodium methylglycine diacetate marketed by BASF under the trade name TRILON M); honey; sugar derivatives such as O-octanoyl-6-D-maltose and N-acetylglucosamine; chestnut extracts such as those marketed by the company SILAB under the name Recoverine®, prickly pear extracts such as those marketed under the name Exfolactive® by the company SILAB, or Phytosphingosine SLC® (phytosphingosine grafted with a salicylic acid) marketed by the company Degussa.

Desquamating agents suitable for the invention may be chosen in particular from the group comprising sulphonic acids, calcium chelators, α-hydroxy acids such as glycolic, citric, lactic, tartaric, malic or mandelic acids; ascorbic acid and its derivatives such as ascorbyl glucoside and magnesium ascorbyl phosphate; nicotinamide; urea; (N-2-hydroxyethylpiperazine-N-2-ethane)sulphonic acid (HEPES), β-hydroxy acids such as salicylic acid and its derivatives, retinoids such as retinol and its esters, retinal, retinoic acid and its derivatives, those described in the documents FR 2570377 A1, EP 0199636 A1, EP 0325540 A1, EP 0402072 A1, chestnut or prickly pear extracts, in particular marketed by SILAB; reducing compounds such as cysteine or cysteine precursors.

Desquamating agents which can be used are also nicotinic acid and its esters and nicotinamide, also called vitamin B3 or vitamin PP, and ascorbic acid and its precursors, as described in particular in application EP 1529522 A1.

Anti-Cellulite Agents.

Anti-cellulite agents and lipolytic agents are preferably selected from the group consisting of those described in WO 2007/077541, and beta-adrenergic receptor agonists such as synephrine and its derivatives, and cyclohexyl carbamates described in WO 2010/097479. Agents enhancing or boosting the activity of anti-cellulite agents, in particular agents which stimulate and/or depolarise C nerve fibres, are preferably selected from the group consisting of capsaicin and derivatives thereof, vanillyl-nonylamid and derivatives thereof, L-carnitine, coenzym A, isoflavonoides, soy extracts, *ananas* extract and conjugated linoleic acid.

Fat Enhancing Agents.

Formulations and products according to the present invention may also comprise one or more fat enhancing and/or adipogenic agents as well as agents enhancing or boosting the activity of fat enhancing agents. A fat enhancing agent is for example hydroxymethoxyphenyl propylmethylmethoxybenzofuran (trade name: Sym3D®).

Hair Growth Activators or Inhibitors

Formulations and products according to the present invention may also comprise one or more hair growth activators, i.e. agents to stimulate hair growth. Hair growth activators are preferably selected from the group consisting of pyrimidine derivatives such as 2,4-diaminopyrimidine-3-oxide (Aminexil), 2,4-diamino-6-piperidinopyrimidine-3-oxide (Minoxidil) and derivatives thereof, 6-amino-1,2-dihydro-1-hydroxy-2-imino-4-piperidinopyrimidine and its derivatives, xanthine alkaloids such as caffeine, theobromine and theophylline and derivatives thereof, quercetin and derivatives, dihydroquercetin (taxifolin) and derivatives, potassium channel openers, antiandrogenic agents, synthetic or natural 5-reductase inhibitors, nicotinic acid esters such as tocopheryl nicotinate, benzyl nicotinate and C1-C6 alkyl nicotinate, proteins such as for example the tripeptide Lys-Pro-Val, diphencypren, hormons, finasteride, dutasteride, flutamide, bicalutamide, pregnane derivatives, progesterone and its derivatives, cyproterone acetate, spironolactone and other diuretics, calcineurin inhibitors such as FK506 (Tacrolimus, Fujimycin) and its derivatives, Cyclosporin A and derivatives thereof, zinc and zinc salts, polyphenols, procyanidins, proanthocyanidins, phytosterols such as for example beta-sitosterol, biotin, eugenol, (±)-beta-citronellol, panthenol, glycogen for example from mussels, extracts from microorganisms, algae, plants and plant parts of for example the genera dandelion (*Leontodon* or *Taraxacum*), *Orthosiphon*, *Vitex*, *Coffea*, *Paullinia*, *Theobroma*, *Asiasarum*, *Cucurbita* or *Styphnolobium*, *Serenoa repens* (saw palmetto), *Sophora flavescens*, *Pygeum africanum*, *Panicum miliaceum*, *Cimicifuga racemosa*, *Glycine max*, *Eugenia caryophyllata*, *Cotinus coggygria*, *Hibiscus rosa-sinensis*, *Camellia sinensis*, *Ilex paraguariensis*, *Isochrysis galbana*, licorice, grape, apple, barley or hops or/and hydrolysates from rice or wheat.

Alternatively, formulations and products according to the present invention may comprise one or more hair growth inhibitors (as described above), i.e. agents to reduce or prevent hair growth. Hair growth inhibitors are preferably selected from the group consisting of activin, activin derivatives or activin agonists, ornithine decarboxylase inhibitors such as alpha-difluoromethylornithine or pentacyclic triterpenes like for example ursolic acid, betulin, betulinic acid, oleanolic acid and derivatives thereof, 5alpha-reductase inhibitors, androgen receptor antagonists, S-adenosylmethionine decarboxylase inhibitors, gamma-glutamyl transpeptidase inhibitors, transglutaminase inhibitors, soybean-derived serine protease inhibitors, extracts from microorganisms, algae, different microalgae or plants and plant parts of for example the families Leguminosae, Solanaceae, Graminae, Asclepiadaceae or Cucurbitaceae, the genera *Chondrus*, *Gloiopeltis*, *Ceramium*, *Durvillea*, *Glycine max*, *Sanguisorba officinalis*, *Calendula officinalis*, *Hamamelis virginiana*, *Arnica montana*, *Salix alba*, *Hypericum perforatum* or *Gymnema sylvestre*.

Cooling Agents

The compositions may also contain one or more substances with a physiological cooling effect (cooling agents), which are preferably selected here from the following list: menthol and menthol derivatives (for example L-menthol, D-menthol, racemic menthol, isomenthol, neoisomenthol, neomenthol) menthylethers (for example (I-menthoxy)-1,2-propandiol, (I-menthoxy)-2-methyl-1,2-propandiol, I-menthyl-methylether), menthylesters (for example menthylformiate, menthylacetate, menthylisobutyrate, menthyllactates, L-menthyl-L-lactate, L-menthyl-D-lactate, menthyl-(2-methoxy)acetate, menthyl-(2-methoxyethoxy) acetate, menthylpyroglutamate), menthylcarbonates (for example menthylpropyleneglycolcarbonate, menthylethyleneglycolcarbonate, menthylglycerolcarbonate or mixtures thereof), the semi-esters of menthols with a dicarboxylic acid or derivatives thereof (for example mono-menthylsuccinate, mono-menthylglutarate, mono-menthylmalonate, O-menthyl succinic acid ester-N,N-(dimethyl)amide, O-menthyl succinic acid ester amide), menthanecarboxylic acid amides (in this case preferably menthanecarboxylic acid-N-ethylamide [WS3] or N$^\alpha$-(menthanecarbonyl)glycinethylester [WS5], as described in U.S. Pat. No. 4,150,052, menthanecarboxylic acid-N-(4-cyanophenyl)amide or menthanecarboxylic acid-N-(4-cyanomethylphenyl)amide as described in WO 2005 049553 A1, methanecarboxylic acid-N-(alkoxyalkyl)amides), menthone and menthone derivatives (for example L-menthone glycerol ketal), 2,3-dimethyl-2-(2-propyl)-butyric acid derivatives (for example 2,3-dimethyl-2-(2-propyl)-butyric acid-N-methylamide [WS23]), isopulegol or its esters (I-(−)-isopulegol, I-(−)-isopulegolacetate), menthane derivatives (for example p-menthane-3,8-diol), cubebol or synthetic or natural mixtures, containing cubebol, pyrrolidone derivatives of cycloalkyldione derivatives (for example 3-methyl-2(1-pyrrolidinyl)-2-cyclopentene-1-one) or tetrahydropyrimidine-2-one (for example iciline or related compounds, as described in WO 2004/026840), further carboxamides (for example N-(2-(pyridin-2-yl)ethyl)-3-p-menthanecarboxamide or related compounds), (1R,2S,5R)—N-(4-Methoxyphenyl)-5-methyl-2-(1-isopropyl)cyclohexane-carboxamide [WS12], oxamates (preferably those described in EP 2033688 A2).

Anti-Microbial Agents

Suitable anti-microbial agents are, in principle, all substances effective against Gram-positive bacteria, such as, for example, 4-hydroxybenzoic acid and its salts and esters, N-(4-chlorophenyl)-N'-(3,4-dichlorophenyl)urea, 2,4,4'-trichloro-2'-hydroxy-diphenyl ether (triclosan), 4-chloro-3, 5-dimethyl-phenol, 2,2'-methylenebis(6-bromo-4-chlorophenol), 3-methyl-4-(1-methylethyl)phenol, 2-benzyl-4-chloro-phenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, oil of cloves, menthol, mint oil, farnesol, phenoxyethanol, glycerol monocaprate, glycerol monocaprylate, glycerol monolaurate (GML), diglycerol monocaprate (DMC), salicylic acid N-alkylamides, such as, for example, n-octylsalicylamide or n-decylsalicylamide.

Enzyme Inhibitors

Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate (Hydagen CAT). The substances inhibit enzyme activity, thereby reducing the formation of odour. Other substances which are suitable esterase inhibitors are sterol sulfates or phosphates, such as, for example, lanosterol, cholesterol, campesterol, stigmasterol and sitosterol sulfate or phosphate, dicarboxylic acids and esters thereof, such as, for example, glutaric acid, monoethyl glutarate, diethyl glutarate, adipic acid, monoethyl adipate, diethyl adipate, malonic acid and diethyl malonate, hydroxycarboxylic acids and esters thereof, such as, for example, citric acid, malic acid, tartaric acid or diethyl tartrate, and zinc glycinate.

Odour Absorbers and Antiperspirant Active Agents

Suitable odour absorbers are substances which are able to absorb and largely retain odour-forming compounds. They lower the partial pressure of the individual components, thus also reducing their rate of diffusion. It is important that perfumes must remain unimpaired in this process. Odour absorbers are not effective against bacteria. They comprise, for example, as main constituent, a complex zinc salt of ricinoleic acid or specific, largely odour-neutral fragrances which are known to the person skilled in the art as "fixatives", such as, for example, extracts of labdanum or *styrax* or certain abietic acid derivatives. The odour masking agents are fragrances or perfume oils, which, in addition to their function as odour masking agents, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also suitable are animal products, such as, for example, civet and castoreum. Typical synthetic fragrance compounds are products of the ester, ether, aldehyde, ketone, alcohol, and hydrocarbon type. Fragrance compounds of the ester type are, for example, benzyl acetate, p-tert-butylcyclohexyl acetate, linalyl acetate, phenylethyl acetate, linalyl benzoate, benzyl formate, allyl cyclohexylpropionate, styrallyl propionate and benzyl salicylate. The ethers include, for example, benzyl ethyl ether, and the aldehydes include, for example, the linear alkanals having 8 to 18 carbon atoms, citral, citronellal, citronellyloxyacetaldehyde, cyclamen aldehyde, hydroxycitronellal, lilial and bourgeonal, the ketones include, for example, the ionones and methyl cedryl ketone, the alcohols include anethole, citronellol, eugenol, isoeugenol, geraniol, linaool, phenylethyl alcohol and terpineol, and the hydrocarbons include mainly the terpenes and balsams. Preference is, however, given to using mixtures of different fragrances which together produce a pleasing fragrance note. Essential oils of relatively low volatility, which are mostly used as aroma components, are also suitable as perfume oils, e.g. sage oil, camomile oil, oil of cloves, melissa oil, mint oil, cinnamon leaf oil, linden flower oil, juniperberry oil, vetiver oil, olibanum oil, *galbanum* oil, labdanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Suitable astringent antiperspirant active ingredients are primarily salts of aluminium, zirconium or of zinc. Such suitable antihydrotic active ingredients are, for example, aluminium chloride, aluminium chlorohydrate, aluminium dichlorohydrate, aluminium sesquichlorohydrate and complex compounds thereof, e.g. with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, e.g. with amino acids, such as glycine.

Film Formers and Anti-Dandruff Agents

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Suitable antidandruff agents are Pirocton Olamin (1-hydroxy-4-methyl-6-(2,4,4-trimethylpentyl)-2-(1H)-pyridinone monoethanolamine salt), Baypival® (Climbazole), Ketoconazol® (4-acetyl-1-{4-[2-(2,4-dichlorophenyl) r-2-(1H-imidazol-1-ylmethyl)-1,3-dioxylan-c-4-ylmethoxyphenyl}-piperazine, ketoconazole, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminium pyrithione and magnesium pyrithione/dipyrithione magnesium sulfate.

Carriers and Hydrotropes

Preferred cosmetics carrier materials are solid or liquid at 25° C. and 1013 mbar (including highly viscous substances) as for example glycerol, 1,2-propylene glycol, 1,2-butylene glycol, 1,3-propylene glycol, 1,3-butylene glycol, ethanol, water and mixtures of two or more of said liquid carrier materials with water. Optionally, these preparations according to the invention may be produced using preservatives or solubilizers. Other preferred liquid carrier substances, which may be a component of a preparation according to the invention are selected from the group consisting of oils such as vegetable oil, neutral oil and mineral oil.

Preferred solid carrier materials, which may be a component of a preparation according to the invention are hydrocolloids, such as starches, degraded starches, chemically or physically modified starches, dextrins, (powdery) maltodextrins (preferably with a dextrose equivalent value of 5 to 25, preferably of 10-20), lactose, silicon dioxide, glucose, modified celluloses, gum arabic, ghatti gum, traganth, karaya, carrageenan, pullulan, curdlan, xanthan gum, gellan gum, guar flour, carob bean flour, alginates, agar, pectin and inulin and mixtures of two or more of these solids, in particular maltodextrins (preferably with a dextrose equivalent value of 15-20), lactose, silicon dioxide and/or glucose.

In addition, hydrotropes, for example ethanol, isopropyl alcohol or polyols, may be used to improve flow behaviour. Suitable polyols preferably contain 2 to 15 carbon atoms and at least two hydroxyl groups. The polyols may contain other functional groups, more especially amino groups, or may be modified with nitrogen. Typical examples are glycerol;
alkylene glycols such as, for example, ethylene glycol, diethylene glycol, propylene glycol, butylene glycol, hexylene glycol and polyethylene glycols with an average molecular weight of 100 to 1000 Dalton;
technical oligoglycerol mixtures with a degree of self-condensation of 1.5 to 10, such as for example technical diglycerol mixtures with a diglycerol content of 40 to 50% by weight;
methylol compounds such as, in particular, trimethylol ethane, trimethylol propane, trimethylol butane, pentaerythritol and dipentaerythritol;
lower alkyl glucosides, particularly those containing 1 to 8 carbon atoms in the alkyl group, for example methyl and butyl glucoside;
sugar alcohols containing 5 to 12 carbon atoms, for example sorbitol or mannitol,
sugars containing 5 to 12 carbon atoms, for example glucose or sucrose;
amino sugars, for example glucamine;
dialcoholamines, such as diethanolamine or 2-aminopropane-1,3-diol.

Preservatives

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive").

Perfume Oils and Fragrances

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, *angelica*, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (*galbanum*, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, alpha-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, *galbanum* oil, *ladanum* oil and lavendin oil. The following are preferably used either individually or in the form of mixtures: bergamot oil, dihydromyrcenol, lilial, lyral, citronellol, phenylethyl alcohol, hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Dyes

Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). Luminol may also be present as a luminescent dye. Advantageous coloured pigments are for example titanium dioxide, mica, iron oxides (e.g. $Fe_2O_3$ $Fe_3O_4$, FeO(OH)) and/or tin oxide. Advantageous dyes are for example carmine, Berlin blue, chromium oxide green, ultramarine blue and/or manganese violet.

Preparations

Preferred compositions according to the present inventions are selected from the group of products for treatment, protecting, care and cleansing of the skin and/or hair or as a make-up product, preferably as a leave-on product (meaning that the one or more compounds of formula (I) stay on the skin and/or hair for a longer period of time, compared to rinse-off products, so that the moisturizing and/or anti-ageing and/or wound healing promoting action thereof is more pronounced).

The formulations according to the invention are preferably in the form of an emulsion, e.g. W/O (water-in-oil), O/W (oil-in-water), W/O/W (water-in-oil-in-water), O/W/O (oil-in-water-in-oil) emulsion, PIT emulsion, Pickering emulsion, emulsion with a low oil content, micro- or nanoemulsion, a solution, e.g. in oil (fatty oils or fatty acid esters, in particular $C_6$-$C_{32}$ fatty acid $C_2$-$C_{30}$ esters) or silicone oil, dispersion, suspension, creme, lotion or milk, depending on the production method and ingredients, a gel (including hydrogel, hydrodispersion gel, oleogel), spray (e.g. pump spray or spray with propellant) or a foam or an impregnating solution for cosmetic wipes, a detergent, e.g. soap, synthetic detergent, liquid washing, shower and bath preparation, bath product (capsule, oil, tablet, salt, bath salt, soap, etc.), effervescent preparation, a skin care product such as e.g. an emulsion (as described above), ointment, paste, gel (as described above), oil, balsam, serum, powder (e.g. face powder, body powder), a mask, a pencil, stick, roll-on, pump, aerosol (foaming, non-foaming or post-foaming), a deodorant and/or antiperspirant, mouthwash and mouth rinse, a foot care product (including keratolytic, deodorant), an insect repellent, a sunscreen, aftersun preparation, a shaving product, aftershave balm, pre- and aftershave lotion, a depilatory agent, a hair care product such as e.g. shampoo (including 2-in-1 shampoo, anti-dandruff shampoo, baby shampoo, shampoo for dry scalps, concentrated shampoo), conditioner, hair tonic, hair water, hair rinse, styling creme, pomade, perm and setting lotion, hair spray, styling aid (e.g. gel or wax), hair smoothing agent (detangling agent, relaxer), hair dye such as e.g. temporary direct-dyeing hair dye, semi-permanent hair dye, permanent hair dye, hair conditioner, hair mousse, eye care product, make-up, make-up remover or baby product.

The formulations according to the invention are particularly preferably in the form of an emulsion, in particular in the form of a W/O, O/W, W/O/W, O/W/O emulsion, PIT emulsion, Pickering emulsion, emulsion with a low oil content, micro- or nanoemulsion, a gel (including hydrogel, hydrodispersion gel, oleogel), a solution e.g. in oil (fatty oils or fatty acid esters, in particular $C_6$-$C_{32}$ fatty acid $C_2$-$C_{30}$ esters)) or silicone oil, or a spray (e.g. pump spray or spray with propellant).

Auxiliary substances and additives can be included in quantities of 5 to 99% b.w., preferably 10 to 80% b.w., based on the total weight of the formulation. The amounts of cosmetic or dermatological auxiliary agents and additives and perfume to be used in each case can easily be determined by the person skilled in the art by simple trial and error, depending on the nature of the particular product.

The preparations can also contain water in a quantity of up to 99% b.w., preferably 5 to 80% b.w., based on the total weight of the preparation.

Non-Pharmaceutical Applications

In addition, the invention is also directed to a number of applications, in particular to the use of the extracts of the Chenopodiaceae *Halimione portulacoides*
  for the treatment of human hair;
  for the treatment of human skin;
  for modulating melanogenesis in human hair and/or human skin;
  for the growth of human hair and hair follicles;
  for combating and preventing hair loss;
  for preventing and combating skin aging; for improving and stimulating the synthesis of the extracellular matrix in the human dermis;
  for improving and stimulating collagen synthesis in the human dermis;
  for modulating keratinocyte differentiation in the human epidermis;
  for modulating the horny layer in the human epidermis;
  for modulating the synthesis and secretion of sebum;
  for modulating lipogenesis;
  for preventing or inhibiting skin inflammation.

All these applications can be summarized using the expression "modulation" of human skin and human hair, in order to combat or prevent symptoms like hair loss or hair de-pigmentation or skin conditions associated with aging and certain dysfunctions of the hair follicles such as, for example, pimples or inflammation.

Pharmaceutical Applications

Mutatis-mutandis the foregoing applies also to pharmaceutical activities of the extracts. Therefore additional embodiments of the present invention are directed to pharmaceutical compositions comprising extracts of *Halimione* sp.

for use in the treatment human skin and hair;
for use in the improvement sebum production;
for use in the modulation of growth of human hair;
for use in the prevention and fight against hair loss;
for use in the prevention and fight against skin aging;
for use in the improvement and stimulation of collagen synthesis in the human dermis;
for use in the improvement and stimulation of glucosaminoglycans synthesis;
for use in the modulation of differentiation in the human epidermis;
for use in the modulation of the horny layer in the human epidermis; and
for use in the modulation of the adipocyte metabolism.

In the following, the invention is illustrated by—but not limited to—some working examples.

EXAMPLES

General Remarks

The extraction protocols were selected from many other technical solutions, and should be considered as truly exemplificative representations. According to the present invention, freshly harvested plants were minced and extracted with a liquid extractant selected from the group consisting of ethyl acetate, isopropanol, ethanol, methanol and water. Since the alcoholic solvents extract also part of the water present in the fresh biomass, the resulting extract have to be regarded as hydro-alcoholic.

The extractant can also comprise a mixture of two or more of the above solvents. The extraction yields in dry weight, expressed as percentage of the fresh weight of the plant material, are reported in Table 1. As the composition of the plants may change in relation to several environmental conditions, the extraction efficacy may also change and the extract dry weights have to be considered as rough indications.

Finally, quantity and quality of compounds present in the extracts may vary with respect to both solvent properties and preparation protocol.

TABLE 1

Dry weight of the extracts expressed as percentage of the fresh weight of *Halimione portulacoides*

| Extractant | Extract yield |
| --- | --- |
| Water | 11%-12% |
| Methanol | 4.8%-5.2% |
| Ethanol | 4.9% |

TABLE 1-continued

Dry weight of the extracts expressed as percentage of the fresh weight of *Halimione portulacoides*

| Extractant | Extract yield |
| --- | --- |
| Isopropyl alcohol | 4.4% |
| Ethyl acetate | 0.3% |

Activity of the Extracts on Hair Follicle Growth

Examples 1 to 2

Activity on the Growth of Hair Follicles of Methanol (MeOH) Extract Obtained from *Halimione portulacoides* Harvested in Autumn Hair follicles were taken from a single donor's scalp sample and transferred into sterile 24-well plates to be cultivated using a modified Williams' Medium E. Cultivation took place for nine days, while the experimental treatment of the follicles began 24 hours after the start of the cultivation. Hair follicles were selected for the experiments after 18 h of cultivation. Only those follicles showing a good vital stage and a growth of not less than 0.2 mm were considered suitable to be maintained in culture. All experimental groups and the control were prepared comprising 12-18 follicles, plated in 24-well plates at a density of 3 hair follicles/well. Hair follicles showing evident signs of suffering during the culture for reasons not dependent on the experimental treatment were excluded from the final analysis. The following experiment was conducted to demonstrate the activity on hair follicle growth of the methanol extract (MeOH) obtained from *Halimione portulacoides* harvested in autumn. The extract was dried under vacuum and then dissolved in 50% DMSO at the final concentration of 20,000 µg/ml. 0.5 µl/ml or 0.05 µl/ml of this stock solution was added to the culture medium in order to obtain the final supplementation with extract at 10 µg/ml and 1 µg/ml, respectively.

The growth performances observed in the treated hair follicles were compared to a control group cultured in the same culture medium free of extract supplement. The activity of the treatment was demonstrated by an increase in growth of the hair follicles expressed as a variation of the average elongation of the experimental groups in comparison to the control group (Table 2). The experiment was terminated after 9 days of cultivation (8 of treatment). The growth of the hair follicles was studied by microphotography and subsequently determined by image analysis. All hair follicles were photographed at day 5 and day 9 of culture, respectively.

TABLE 2

Growth of hair follicles. Elongation expressed as % ratio of the control group performance. The statistical significance has been evaluated by means of ANOVA (Analysis of Variance, LSD test)

| Example | Sample | Amount | Average | Total no. of HFs | ANOVA |
| --- | --- | --- | --- | --- | --- |
| 0 | Control | 0 | 100.0 ± 6.3 | 11 | |
| 1 | MeOH | 1.0 µg/ml | 111.3 ± 4.6 | 9 | n.s. |
| 2 | MeOH | 10.0 µg/ml | 100.1 ± 7.7 | 9 | n.s. |

The treatment performed with 1 µg/ml of extract increased the follicle elongation by 11%. Although this response does not reach the threshold of significance for statistical purposes, the detected growth increment is comparable to that produced by well-known stimulants, such as insulin (+10%) or cyclosporine-a (+12%). As a general rule, the intensity of the response depends on the sensitivity of the donor as well as the intensity of the stimulus. These results show that the addition of the methanol extract leads to an increase in growth of the hair follicles in comparison to the untreated group.

Examples 3 to 4

Activity on the Growth of Hair Follicles of Methanol (MeOH) Extract Obtained from *Halimione portulacoides* Harvested in Spring The experimental protocol previously described was adopted to study the activity of a methanolic extract obtained from *Halimione portulacoides* harvested in spring. The experiment was replicated twice. Both donors responded to the treatment and the results shown in Table 3 were computed by pooling the data recorded from both replicates.

TABLE 3

Growth of hair follicles. Elongation expressed as % ratio of the control group performance. Data pooled from 2 donors (responsiveness = 100%). The statistical significance has been evaluated by means of ANOVA (Analysis of Variance, LSD test)

| Example | Sample | Amount | Average | Total no. of HFs | ANOVA |
|---|---|---|---|---|---|
| 0 | Control | 0 | 100.0 ± 3.4 | 25 | |
| 3 | MeOH | 1.0 µg/ml | 107.4 ± 3.8 | 23 | n.s. |
| 4 | MeOH | 10.0 µg/ml | 120.6 ± 4.2 | 21 | P < 0.01 |

The results indicate that the addition of the methanol extract stimulates the growth of the hair follicles, with intensity varying from 7.4% to 20.6% in comparison to the untreated group. The best response was obtained by treating the hair follicle with 10 µg/ml of extract and the resulting increase of hair elongation is highly significant on a statistical basis.

Examples 5 to 16

Activity of Various *Halimione* Extracts on the Growth of Hair Follicles

The experimental protocol previously described was adopted to study the activity of some extracts obtained from *Halimione portulacoides* by means of different solvents: methanol (MeOH), ethyl acetate (EtAc), ethanol (EtOH) and isopopanol (IsopOH). The biological activity of these alternative preparations was compared by treating groups of hair follicles microdissected from a single scalp sample.

Organ culture and supplementation of the culture media were performed as reported for the previous experiments. The variation of growth performance expressed by each group compared to the control is reported in Table 4.

TABLE 4

Growth of hair follicles. Elongation expressed as % ratio of the control group performance. The statistical significance has been evaluated by means of ANOVA (Analysis of Variance, LSD test)

| Example | Sample | Amount | Average | Total no. of HFs | ANOVA |
|---|---|---|---|---|---|
| 0 | Control | 0 | 100.0 ± 4.0 | 18 | |
| 5 | EtAc | 0.1 µg/ml | 97.4 ± 6.0 | 11 | n.s. |
| 6 | EtAc | 1.0 µg/ml | 123.1 ± 6.8 | 10 | P < 0.01 |
| 7 | EtAc | 10.0 µg/ml | 118.0 ± 6.8 | 10 | P < 0.01 |
| 8 | IsopOH | 0.1 µg/ml | 116.3 ± 7.0 | 11 | P < 0.05 |
| 9 | IsopOH | 1.0 µg/ml | 114.2 ± 7.8 | 9 | n.s. |
| 10 | IsopOH | 10.0 µg/ml | 116.0 ± 6.8 | 9 | n.s. |
| 11 | EtOH | 0.1 µg/ml | 112.4 ± 6.5 | 12 | n.s. |
| 12 | EtOH | 1.0 µg/ml | 129.0 ± 7.5 | 10 | P < 0.01 |
| 13 | EtOH | 10.0 µg/ml | 119.4 ± 3.5 | 11 | P < 0.05 |
| 14 | MeOH | 0.1 µg/ml | 122.7 ± 7.0 | 11 | P < 0.01 |
| 15 | MeOH | 1.0 µg/ml | 110.4 ± 6.4 | 11 | n.s. |
| 16 | MeOH | 10.0 µg/ml | 101.7 ± 5.9 | 11 | n.s. |

The results obtained attest that all the tested preparations stimulated the hair growth, producing an increase in elongation ranging from 10% to 29%. All the extracts, at certain concentrations, produced significant (P<0.05) or very significant (P<0.01) stimulations on a statistical basis.

Conclusions

The reported examples attest to the intense activity of the studied extracts on the metabolism of hair follicles. All results show that *Halimione portulacoides* is a valid source of active compounds, suitable for stimulating hair growth. The increased hair growth, in culture conditions, can be achieved by improving the general wellness of the organ and/or by delaying the catagen, which occurs physiologically when the follicle is explanted from the scalp. Both these effects are strongly desirable and make the extracts very interesting for cosmetic applications, in particular as ingredient for preparations aimed at combating hair loss.

Hair growth stimulations were obtained with extracts prepared from plants harvested at the beginning and end of the annual vegetative cycle. This attests that the active compounds are stably synthesized by plants.

The experiment performed comparing different extracts attests that the active compounds can be extracted from the plant by using different solvents. However, it is also probable that the tested extracts differed from one another with regard to combination and composition of active ingredients, therefore the detected responses, even if similar, might be produced by different compounds.

The detected stimulation has to be regarded as very intense, since the increase of hair growth usually recorded in response to treatments with positive controls (e.g. insulin and cyclosporine-a) can indicatively vary between 10% and 15%.

Activity on Melanogenesis

Melanocytes are the cell species responsible for melanogenesis in both skin and hair follicles. Melanin is the pigment accumulated in hair and skin and susceptible to be quantitatively modulated in response to sunlight exposure, aging processes and also to pathological events.

The possibility of modulating melanogenesis therefore represents a significant opportunity in cosmetics, due to the importance that physical appearance assumes in social life, but also for the effective preservation of healthy and youthful-looking skin and hair.

The activity of the *Halimione* extracts on melanogenesis was studied by screening them on ex-vivo human skin cultures, in order to also attest the effect in vivo.

Assay Performed on Ex-Vivo Human Skin Culture

Organ cultures of ex-vivo human skin were performed starting from a skin sample, exciding cylindrical pieces of about 7 mm in diameter and culturing them up to day 6. The culture medium was a modified William-E, and was renewed at day three of the tissue culture. Samples of the extracts were air-dried and then dissolved in a quantity of 50% DMSO suitable to obtain a final concentration of 1 and 10 µg/ml or, as an alternative, 5 and 50 µg/ml. On a daily basis, 4 µl of these extract preparations were applied topically to the cultured skin samples. After six days of organ culture, histological sections were prepared from the skin samples, and quantitative changes of melanin content were investigated by the Fontana-Masson staining technique. The melanin quantification was obtained by image analysis of the microphotographs of each histological skin section.

Examples 17 to 18

Activity on Melanogenesis of Methanolic Extract Obtained from *Halimione portulacoides* Harvested in Spring In spring, plants of *Halimione portulacoides* were harvested and immediately prepared for the extraction process. Tender branches and leaves were finely minced and extracted with methanol. This extract was screened by treating human skin samples as described above. The results are shown in Table 5.

TABLE 5

Modulation of melanogenesis, evaluated in ex-vivo cultured human skin, following treatment with methanol extract obtained from *Halimione portulacoides*, harvested in spring. Melanin content is expressed as % ratio of the control group performance. The statistical significance was evaluated by means of ANOVA (Analysis of Variance, LSD test)

| Example | Sample | Amount | Average | No. of samples | ANOVA |
|---|---|---|---|---|---|
| 0 | Control | 0 | 100.0 ± 6.4 | 24 | |
| 17 | MeOH | 1.0 µg/ml | 151.1 ± 14.4 | 12 | P < 0.01 |
| 18 | MeOH | 10 µg/ml | 136.3 ± 17.0 | 11 | P < 0.05 |

The results attest that the treatment intensely stimulated the melanogenesis. The increase in melanin content varied from +36% to 51%, which represent very high responses, respectively significant or very significant on a statistical basis.

Examples 19 to 22

Activity on Melanogenesis of Methanolic Extract Obtained from *Halimione portulacoides* Harvested in Autumn

*Halimione portulacoides* produces fruit in autumn, so plants were harvested in this season, then tender branches and leaves were separated from fruits. These two different plant materials were prepared as usual and then separately extracted using methanol.

The obtained extracts were screened by treating human skin samples as described above. The experiment was replicated twice using skin samples taken from two donors. The results shown in Table 6 were computed by pooling the data recorded from both replicates.

TABLE 6

Modulation of melanogenesis, evaluated in ex-vivo cultured human skin, following treatment with methanol extracts of branches + leaves (BL) and fruits (F), obtained from *Halimione portulacoides* harvested in autumn. Melanin content expressed as % ratio of the control group performance. Data pooled from two donors. The statistical significance was evaluated by means of Krustal Wallis test followed by Games-Howell test.

| Ex. | Extract-ant | Sample | Amount | Average | No. Of samples | ANOVA |
|---|---|---|---|---|---|---|
| 0 | | Control | 0 | 100.0 ± 5.5 | 47 | |
| 19 | MeOH | BL | 1.0 µg/ml | 135.9 ± 9.8 | 24 | P < 0.05 |
| 20 | MeOH | BL | 10 µg/ml | 159.6 ± 13.8 | 24 | P < 0.01 |
| 21 | MeOH | F | 1.0 µg/ml | 120.0 ± 8.5 | 24 | n.s. |
| 22 | MeOH | F | 10 µg/ml | 154.1 ± 10.8 | 24 | P < 0.01 |

Both the extracts strongly stimulated the production of melanin in the skin. The increase of melanin content in the treated samples ranged between +20% and +60% compared to the control. Both the tested donors responded to the treatments and the results obtained are highly significant on a statistical basis for both the extracts.

The examples 17-22 attest that *Halimione portulacoides* synthesizes one or more compounds very active on skin melanogenesis, suitable to be exploited as a powerful skin darkener. The active compounds are produced throughout the vegetative season and are present in all the aerial parts of the plant, including fruits.

Examples 23 to 30

Activity on Melanogenesis of Various Extracts Obtained from *Halimione portulacoides* Harvested in Spring In spring, plants of *Halimione portulacoides* were harvested and immediately prepared for the extraction process. Tender branches and leaves were finely minced and extracted by means of different solvents: ethyl acetate (EtAc), ethanol (EtOH), methanol (MeOH) and water (Water).

These extracts were screened by treating human skin samples as previously described. The results are shown in Table 7:

TABLE 7

Modulation of melanogenesis, evaluated in ex-vivo cultured human skin following treatment with extracts obtained from *Halimione portulacoides* harvested in spring. The extracts were prepared using different extractants: ethyl acetate (EtAc), ethanol (EtOH), methanol (MeOH) and water (Water). Melanin content expressed as % ratio of the control group performance. The statistical significance was evaluated by means of One-way anova with permutation test followed by pairwise post-hoc comparisons - Dunnett's permutation test

| Example | Sample | Amount | Average | No. of samples | ANOVA |
|---|---|---|---|---|---|
| 0 | Control | 0 | 100.0 ± 5.9 | 24 | |
| 23 | EtAc | 5.0 µg/ml | 171.3 ± 26.2 | 12 | P < 0.01 |
| 24 | EtAc | 50 µg/ml | 139.6 ± 11.0 | 12 | P < 0.05 |
| 25 | EtOH | 5.0 µg/ml | 175.3 ± 8.8 | 12 | P < 0.01 |
| 26 | EtOH | 50 µg/ml | 154.9 ± 16.5 | 12 | P < 0.01 |
| 27 | MeOH | 5.0 µg/ml | 164.2 ± 15.2 | 12 | P < 0.01 |
| 28 | MeOH | 50 µg/ml | 125.1 ± 11.9 | 12 | n.s. |
| 29 | Water | 5.0 µg/ml | 153.1 ± 13.0 | 12 | P < 0.01 |
| 30 | Water | 50 µg/ml | 118.8 ± 12.5 | 12 | n.s. |

The results attest that all the treatments intensely stimulated melanogenesis. Interestingly, the increase in melanin content invariably resulted higher at 5 µg/ml than at 50 µg/ml.

Activity on Primary Skin Cells

Extracts of *Halimione portulacoides* were screened for their activity on primary fibroblasts or keratinocytes isolated from human skin. The aim of the screening was to investigate potential activities of stimulation on collagen type I. Collagen is a protein of the dermis which undergoes significant quantity and quality reductions as an effect of skin aging, compromising plumpness, fullness and firmness of the skin. Collagen can be regarded as key indicator of a general anti-aging effect produced by cosmetic treatments.

Modulation of Collagen Synthesis Studied by Means of Primary Dermal Fibroblasts

The experimental procedure was based on the following steps:

Primary fibroblasts were seeded in 96-well microplates at a density of 20,000 cells/cm$^2$;

After 6 h of cultivation, the culture medium was replaced with supplemented culture media prepared by adding 0.1 µg/ml, 1.0 µg/ml or 10 µg/ml of extracts obtained from fruits of *Halimione portulacoides*. A series of 8 wells were used for the screening of each supplemented medium while other 8 wells were maintained as a control group cultured in standard medium.

After 48 h of cultivation, the fibroblasts were close to confluence and the collagen was quantified by means of ELISA directly on the culture plate. The ELISA protocol was specifically set up for these experiments, however, a conceptually similar procedure was reported by Jenkins et al. (2007, BMC Cardiovascular Disorders, 7: 13). The data obtained from the treated groups were expressed as percentage ratio of the values expressed by the control group.

Examples 31 to 33

Activity of Methanol (MeOH) Extract Obtained from Fruits of *Halimione portulacoides* on Fibroblast Collagen Synthesis The MeOH extract obtained from fruits of *Halimione portulacoides* was screened in order to assess its modulating effect on collagen synthesis by dermal fibroblasts. The extract solvent was evaporated and the dry residual solved in 50% DMSO in order to obtain a concentrated stock suitable to supplement the experimental medium without to exceed 0.1% of DMSO. The control medium was supplemented with equivalent volume of 50% DMSO.

Primary fibroblasts were treated as described above and, unpredictably, a relevant collagen synthesis modulation was detected in response to the treatments. The results are shown in Table 8.

TABLE 8

Activity on the dermis detected by treating primary fibroblasts with MeOH extract obtained from fruits of *Halimione portulacoides* at 0.1, 1.0 and 10 µg/ml - Quantity of collagen expressed as % ratio of the value detected for the control group. Statistical significance was evaluated by means of ANOVA (Analysis of Variance, LSD test)

| Example | Sample | Amount | Average | No. of wells | ANOVA |
|---|---|---|---|---|---|
| 0 | Control | 0 | 100.0 ± 2.7 | 8 | |
| 31 | MeOH | 0.1 µg/ml | 107.8 ± 5.3 | 8 | n.s. |
| 32 | MeOH | 1.0 µg/ml | 106.4 ± 3.9 | 8 | n.s. |
| 33 | MeOH | 10 µg/ml | 115.6 ± 4.0 | 8 | P < 0.01 |

The treatment with 10 µg/ml extract increased the collagen synthesis performed by fibroblasts by 16% compared to the control group. The result is highly significant on a statistical basis.

Examples 34 to 36

Activity of Methanol (MeOH) Extract Obtained from Branches and Leaves of *Halimione portulacoides* on Fibroblast Collagen Synthesis Branches and leaves of *Halimione portulacoides* were extracted with methanol as previously described and the obtained extract (MeOH) was screened in order to assess its modulating effect on collagen synthesis by dermal fibroblasts. Primary fibroblasts were treated as described above and, unpredictably, a relevant collagen synthesis modulation was detected in response to the treatments. The results are shown in table 9.

TABLE 9

Activity on the dermis detected by treating primary fibroblasts with MeOH extract obtained from branches and leaves of *Halimione portulacoides* at 2.5, 25 and 250 µg/ml - Quantity of collagen expressed as % ratio of the control group. The statistical significance was evaluated by means of ANOVA (Analysis of Variance, LSD test)

| Example | Sample | Amount | Average | No. of wells | ANOVA |
|---|---|---|---|---|---|
| 0 | Control | 0 | 100.0 ± 4.2 | 8 | |
| 34 | MeOH | 2.5 µg/ml | 104.5 ± 5.7 | 8 | n.s. |
| 35 | MeOH | 25 µg/ml | 101.5 ± 6.8 | 8 | n.s. |
| 36 | MeOH | 250 µg/ml | 122.1 ± 8.4 | 8 | P < 0.05 |

The treatment with 250 µg/ml extract increased the collagen synthesis performed by fibroblasts by 22% compared to the control group. The result is significant on a statistical basis.

Examples 34 to 36

Activity of Ethyl Acetate (EtAc), Ethanol (EtOH) and Methanol (MeOH) Extracts Obtained from Branches and Leaves of *Halimione portulacoides* on Fibroblast Collagen Synthesis Branches and leaves of *Halimione portulacoides* were extracted, as previously described, with three alternative solvents: ethyl acetate (EtAc), ethanol (EtOH) and methanol (MeOH). The biological properties of the obtained extracts were assessed by studying their activity on collagen synthesis by dermal fibroblasts in culture. Primary fibroblasts were treated as described above and a relevant collagen synthesis modulation was detected in response to all the extracts. The results are shown in Table 10.

TABLE 10

Activity on the dermis detected by treating primary fibroblasts with EtAc, EtOH and MeOH extract obtained from branches and leaves of *Halimione portulacoides* at 20, 100 and 500 µg/ml - Quantity of collagen expressed as % ratio of the control group. The statistical significance was evaluated by One-way anova with permutation test followed by pairwise post-hoc comparisons - Dunnett's permutation test

| Example | Sample | Amount | Average | No. of wells | ANOVA |
|---|---|---|---|---|---|
| 0 | Control | 0 | 100.0 ± 1.0 | 6 | |
| 37 | EtAc | 20 µg/ml | 108.4 ± 2.4 | 6 | n.s. |
| 38 | EtAc | 100 µg/ml | 108.3 ± 2.6 | 6 | n.s. |
| 39 | EtAc | 500 µg/ml | 136.1 ± 6.22 | 6 | $P < 0.01$ |
| 40 | EtOH | 20 µg/ml | 108.2 ± 2.3 | 6 | n.s. |
| 41 | EtOH | 100 µg/ml | 117.6 ± 2.2 | 6 | $P < 0.05$ |
| 42 | EtOH | 500 µg/ml | 127.4 ± 10.2 | 6 | $P < 0.01$ |
| 43 | MeOH | 20 µg/ml | 107.7 ± 2.7 | 6 | n.s. |
| 44 | MeOH | 100 µg/ml | 115.4 ± 1.9 | 6 | n.s. |
| 45 | MeOH | 500 µg/ml | 125.1 ± 4.0 | 6 | $P < 0.01$ |

All the extracts stimulated the collagen synthesis by fibroblasts. The treatments at high dosage produced increase of collagen ranging from 17% to 36%. These experimental responses assume statistical relevance according to the adopted test.

Conclusions

The experiments reveal that the extracts obtained from branches, leaves and fruits of *Halimione portulacoides*, contain active compounds suitable to stimulate the collagen synthesis by dermal fibroblasts. This attests that these extracts can be proposed as effective ingredients for anti-aging formulations and for improving the plumpness, fullness and firmness of the skin.

Activity of *Halimione* Extracts on Ex-Vivo Epidermis

The stratum corneum of the skin is the superficial part of the tissue, composed of dead corneocytes, which fulfil the relevant functions of preventing water loss from the skin and the penetration of organisms or undesired compounds from the external environment. The integrity and functionality of the horny layer is essential in order to maintain an appropriate skin moisture and defend the body from pathogens. The skin needs moisture to stay smooth and supple, and the retention of moisture becomes increasingly difficult as the body ages. On the other hand, the altered composition or thickness of the stratum corneum is the cause or part of several common skin disorders, i.e. xerosis, or true pathologies, i.e. psoriasis. Several other unpleasant conditions can be induced by excessive proliferation and differentiation of keratinocytes that result in an excessive turnover and desquamation of the stratum corneum. Typical cases related with this problem are, for instance, dandruff of the scalp and several irritations or inflammatory reactions of the skin, such as contact dermatitis and atopic dermatitis. The term hyperkeratosis generically indicates all the conditions in which the stratum corneum is increased in thickness as a response to several causes. Since hyperkeratosis occurs in a high number of skin disorders, generally related with irritative or inflammatory conditions, there are numerous potential applications of a product that can reduce a hyperproliferative response of the epidermis.

The data reported below attest that the screened *Halimione* extracts can modulate the synthesis of the epidermal stratum corneum. The cell component of the stratum corneum is the corneocyte, which represents the final differentiated stage of the epidermal keratinocyte. Involucrin is a recognized protein marker involved in the keratinization process at the basis of keratinocytes differentiation. Involucrin synthesis can be studied in order to define if an experimental treatment increases or reduces the keratinization of the epidermis. Both these activities can be of interest for applications in cosmetics and therapeutics. The following experiments are aimed at exploring the capability of the extracts to modulate the differentiation of keratinocytes in the skin epidermis by quantifying the involucrin of the stratum corneum via Western Blot analysis (WB).

Activity of *Halimione* Extracts on Involucrin Synthesis Studied on Ex-Vivo Human Skin Culture Examples 46 to 48

Activity of Extracts Obtained from *Halimione* on the Involucrin Synthesis in Cultured Ex-Vivo Skin Three different extracts were prepared from *Halimione*, as already described, by treating the freshly harvested plants with either ethyl acetate (EtAc), ethanol (EtOH) or methanol (MeOH). These extractive solvents were evaporated and the dry residues dissolved in 50% DMSO at the final concentrations of 10 µg/ml. Organ cultures of full thickness human skin were performed starting from a skin sample, exciding cylindrical pieces of about 7 mm in diameter and culturing them up to day 5. Each experimental group included three samples of skin. The culture medium was a modified William-E and was renewed at day 3 of the tissue culture. The cultured skin samples were treated daily by topical application with 4 µl of these *Halimione* preparations diluted in 50% DMSO, while the control received only 50% DMSO. After five days of organ culture, involucrin content of the skin samples was quantified via Western Blot analysis (WB). At the end of the culture the dermis was almost completely removed from the skin samples, while the proteins of the epidermis were extracted. The three skin samples in each experimental group were pooled during the protein extract preparation and, finally, the involucrin content was quantified via WB analysis in five subsamples of the resulting extract.

The tissue responses to the treatments are reported in Table 11 as percentage variation of involucrin content in comparison to the control group. The data shown in the table are the average values obtained from the five replicates of analysis performed for each protein extract and the reported standard errors refer to these averages.

TABLE 11

Activity of extracts obtained from *Halimione* on the involucrin synthesis in cultured ex-vivo human skin - Quantity of involucrin expressed as % ratio of the control group performance

| Ex. | Sample | Amount | Average | Skin samples pooled in the protein extract | Protein extract samples | Response |
|---|---|---|---|---|---|---|
| 0 | Control | 0 | 100 ± 3.1 | 3 | 5 | |
| 46 | EtAc | 10 µg/ml | 104.4 ± 11.0 | 3 | 5 | none |
| 47 | EtOH | 10 µg/ml | 81.0 ± 4.3 | 3 | 5 | inhibition |
| 48 | MeOH | 10 µg/ml | 80.9 ± 1.7 | 3 | 5 | inhibition |

The EtAc extract obtained from *Halimione portulacoides* did not modulate the involucrin synthesis in the epidermis. On the contrary, the two alcohol extracts, i.e. the EtOH and MeOH extracts, produced a 19% inhibition of the involucrin synthesis compared to the control group. These extracts can be adopted in cosmetic or therapeutic compositions formulated to reduce the excessive synthesis of stratum corneum in the various skin conditions described above.

Examples 49 to 54

Activity of Extracts Obtained from *Halimione* on Involucrin Synthesis in Cultured Ex-Vivo Skin In order to confirm the biological activity of the alcohol extracts obtained from *Halimione*, the experiment was repeated by substituting the EtAc extract with the aqueous extract (Water). The ex-vivo skin culture was performed as previously described and the treatments, diluted in 50% DMSO as in the previous experiment, were administered at 1.0 and 10 µg/ml. Also in this experiment the protein extracts were prepared pooling the three skin samples of each experimental group, but the WB analysis was replicated in 6 aliquots sampled from each protein extract. The average values of involucrin content obtained from these analyses, expressed as percentage variation of involucrin content in comparison to the control group, are shown in Table 12.

TABLE 12

Activity of extracts obtained from *Halimione* on involucrin synthesis in cultured ex-vivo human skin - Quantity of involucrin expressed as % ratio of the control group performance

| Ex. | Sample | Amount | Average | Skin samples pooled in the protein extract | Protein extract samples | Response |
|---|---|---|---|---|---|---|
| 0 | Control | 0 | 100.0 ± 10.9 | 3 | 6 | |
| 49 | EtOH | 1.0 µg/ml | 124.4 ± 14.7 | 3 | 6 | stimulation |
| 50 | EtOH | 10 µg/ml | 77.4 ± 8.2 | 3 | 6 | inhibition |
| 51 | MeOH | 1.0 µg/ml | 131.1 ± 14.8 | 3 | 6 | stimulation |
| 52 | MeOH | 10 µg/ml | 68.0 ± 9.0 | 3 | 6 | inhibition |
| 53 | Water | 1.0 µg/ml | 56.5 ± 4.3 | 3 | 6 | inhibition |
| 54 | Water | 10 µg/ml | 69.5 ± 6.6 | 3 | 6 | inhibition |

The results confirm the inhibiting activity of the EtOH and MeOH extracts administered at 10 µg/ml, which reduced the involucrin content by 23% and 32% respectively in comparison to the control group. Surprisingly, the same extracts increased the involucrin content following administration at 1.0 µg/ml. This effect can occur when the extract includes active ingredients having a contrary effect on skin metabolism, but at the same time expressing inverted correlation dosage/effect. As a consequence, the low dosage of extract favours the stimulating ingredient, while increasing the extract dosage the inhibiting ingredient prevails. However, it seems that the stimulating ingredient is moderately lipophilic, while the inhibiting one is hydrophilic. In fact, the aqueous extract reduced the epidermal involucrin at both tested dosages, suggesting that the stimulating ingredient was not included in this extract. As a result, the two active ingredients can be separated in two fractions through chromatography or other suitable process, obtaining from *Halimione* active ingredients both for stimulating and inhibiting the stratum corneum synthesis.

Examples 55 to 59

Activity of Extracts Obtained from *Halimione* on Involucrin Synthesis in Cultured Ex-Vivo Skin In order to confirm the dose-depending activity of the ethanolic extract obtained from *Halimione*, it was performed a new experiment including ethanolic treatments varying between 0.1 and 10 µg/ml. Treatments with aqueous extract at 1 and 10 µg/ml were included too.

The ex-vivo skin culture was performed as previously described and the treatments were diluted in 50% DMSO. Also in this experiment the protein extracts were prepared pooling the three skin samples of each experimental group, the WB analysis was replicated in 3 aliquots sampled from each protein extract. The average values of involucrin content obtained from these analyses, expressed as percentage variation of involucrin content in comparison to the control group, are shown in Table 13.

TABLE 13

Activity of extracts obtained from *Halimione* on involucrin synthesis in cultured ex-vivo human skin - Quantity of involucrin expressed as % ratio of the control group performance

| Ex. | Sample | Amount | Average | Skin samples pooled in the protein extract | Protein extract samples | Response |
|---|---|---|---|---|---|---|
| 0 | Control | 0 | 100.0 ± 3.8 | 3 | 3 | |
| 55 | EtOH | 0.1 µg/ml | 157.6 ± 8.7 | 3 | 3 | stimulation |
| 56 | EtOH | 1 µg/ml | 128.8 ± 7.2 | 3 | 3 | stimulation |
| 57 | EtOH | 10 µg/ml | 106.2 ± 5.1 | 3 | 3 | no response |

TABLE 13-continued

Activity of extracts obtained from *Halimione* on involucrin synthesis in cultured ex-vivo human skin - Quantity of involucrin expressed as % ratio of the control group performance

| Ex. | Sample | Amount | Average | Skin samples pooled in the protein extract | Protein extract samples | Response |
|---|---|---|---|---|---|---|
| 58 | Water | 1.0 µg/ml | 78.5 ± 2.7 | 3 | 3 | inhibition |
| 59 | Water | 10 µg/ml | 110.4 ± 2.1 | 3 | 3 | no response |

The obtained data confirm that the ethanol extract has a stimulating activity at dosage ≤1 µg/ml. In this experiment the stimulating effect almost doubled decreasing the dosage from 1 µg/ml to 0.1 µg/ml. The treatment at 10 µg/ml did not produce any inhibition of involucrin synthesis, however, the stimulation substantially disappeared at this extract concentration.

The aqueous extract confirmed the inhibiting activity previously detected, despite the treatment at 10 µg/ml produced an apparent stimulation without any statistical significance.

Activity of *Halimione* Extracts on Skin Inflammation

Skin inflammation is a common problem which can occur in response to many causes. It can appear as occasional rashes accompanied by skin itching and redness, to chronic conditions such as dermatitis (eczema), rosacea, seborrheic dermatitis, and psoriasis.

The simple application of cosmetics is also sometimes sufficient to trigger an inflammatory reaction. This can occur because the preparation includes irritant compounds, and in this case the inflammatory reaction is quite fast, or as consequence of sensitizers, in which case the stimulus has to be repeated several times before the inflammatory reaction is observed. In both the cases, the inflammatory reaction requires the release of IL-1α from keratinocytes and therefore this cytokine is the ideal marker adopted for screening compounds having potential anti-inflammatory activity.

The following examples shows that the extracts obtained from *Halimione* have a potent anti-inflammatory activity attested by the capacity to inhibit the IL-1α in skin samples treated with a typical irritant stimulus. This valuable effect, combined with the several beneficial activities already discovered with regard to the hair follicle and skin, makes the *Halimione* extracts ideal candidates for cosmetic products as well as potential candidates for therapeutic applications.

Examples 60 to 67

Activity of Extracts Obtained from *Halimione* on Skin Inflammation (IL-1α Release) in Cultured Ex-Vivo Skin In order to study the biological activity of the extracts from *Halimione* on the inflammatory response of skin to irritation, the experimental protocol summarized below was adopted: Ex-vivo skin samples (7 mm in diameter) were cultivated for 24 hours in 6-well plates (4 skin samples/well) with 2.5 ml/well of modified Williams E medium. The experimental design included the following experimental groups, each comprising 8 skin samples cultivated in 2 wells:

control samples cultivated without receiving any stimulus or treatment;
samples stimulated with 2% SDS without subsequent lenitive treatment (negative control);
2 groups of samples stimulated with 2% SDS and then treated with MeOH extract at 1 and 10 µg/ml respectively;
2 groups of samples stimulated with 2% SDS and then treated with EtOH extract at 1 and 10 µg/ml respectively;
2 groups of samples stimulated with 2% SDS and then treated with Water extract at 1 and 10 µg/ml respectively;
samples stimulated with 2% SDS and then treated with dexamethasone at 10 WI (positive control).

After 24 hours of culture the culture medium was renewed and the skin samples 2 to 6 received the irritant stimulus (2% SDS) through topical application of 4 µl of preparation on each skin sample. After 3 hours the stimulus was removed by means of cotton buds and then 4 µl of extract or dexamethasone were topically administered to the groups 3 to 6. Stimulus and lenitive treatments were diluted in 50% DMSO.

After a further 24 hours of cultivation, the culture media were separately collected from each group and the released IL-1α quantified via ELISA (BioLegend ELISAMAX cat. n. 434905).

Table 14 reports the average values of IL-1α obtained from the two medium samples (4 skin samples/well) collected for each experimental group.

TABLE 14

Activity of extracts obtained from *Halimione* on the IL-1α released by ex-vivo human skin samples stimulated with 2% SDS.

| Ex. | Sample | SDS Amount (stimulus) | Treatment Amount (lenitive) | IL-1α (pg/ml) |
|---|---|---|---|---|
| 0 | Control | 0 | 0 | 1.3 |
| 60 | SDS | 2% | 0 | 14.8 |
| 61 | EtOH | 2% | 1.0 µg/ml | 6.4 |
| 62 | EtOH | 2% | 10 µg/ml | 7.4 |
| 63 | MeOH | 2% | 1.0 µg/ml | 6.1 |
| 64 | MeOH | 2% | 10 µg/ml | 10.9 |
| 65 | Water | 2% | 1.0 µg/ml | 10.2 |
| 66 | Water | 2% | 10 µg/ml | 10.3 |
| 67 | Dexam. | 2% | 10 mM | 9.9 |

The results attest that the irritating stimulus produced the expected effect, since the IL-1α released in the medium increased from 1.3 pg/ml to 14.8 pg/ml. Surprisingly, all the treatments with *Halimione* extracts extenuated the inflammatory response, decreasing the IL-1α release by 30% to 60% compared to the SDS group. Interestingly, the extract effect was comparable or superior to the treatment with dexamethasone, a potent steroid glucocorticoid adopted as positive control.

Activity of *Halimione* Extracts on Human Adipocyte Metabolism

Full-thickness ex-vivo human skin samples, including the subcutis, were ex-vivo cultured and treated with different extracts obtained from *Halimione*, in order to evaluate the presence in this plant of natural ingredients active on the lipid metabolism.

The responses of the treated tissues, in comparison to the untreated group, were evaluated after 6 days of culture, by isolating the subcutis of each skin sample and then estimating its normalized content in total lipids.

Examples 68 to 71

Activity of Ethanolic and Aqueous Extracts Obtained from *Halimione* on the Lipid Metabolism of Full-Thickness Skin Two extracts were prepared from freshly harvested *Halimione* plants, as previously described, adopting ethanol and water as solvents. The extracts were prepared at concentrations varying between 8,000 and 11,600 µg/ml and each of these concentrated stocks was directly diluted in culture medium up to the final concentrations of 10 µg/ml and 1 µg/ml. The medium supplemented with ethanolic extract at 10 µg/ml also contained ethanol 0.125%, therefore the same amount of ethanol was added to the other culture media adopted in the experimental design (control and water extract).

Cylindrical pieces (7 mm in diameter) of full thickness human skin were excised from an abdominal skin sample paying attention to preserve the subcutis. These organ samples were seeded in 24-well plates at the density of 1 sample/well with 500 µl of culture medium, and cultured up to day 6. After the first day of culture, the samples were arranged in experimental groups including 4 samples each one. The control group received modified William E medium, while the samples submitted to experimental treatments received the same medium supplemented with the extracts. The culture medium was renewed every other day. After six days of organ culture (five of treatment), the subcutis of each skin sample was separated from the dermis and its total content in lipids and proteins was quantified. The obtained content in lipids was normalized dividing it by the correlated content in proteins (mg lipids/mg proteins), in order to make comparable the values detected in organ samples with different biomass. In fact, stimulation of lipogenesis in the subcutis promotes synthesis and storage of lipids, while it does not substantially affect the metabolism of the structural proteins. As a result, when lipogenesis is stimulated, an increase in the "total lipids/total proteins ratio", hereinafter defined "normalized total lipids", is expected, while the contrary occurs in the case of increased lipolysis.

The analytical protocol adopted to detect values of "normalized total lipids" is described below:

each subcutis sample was homogenized in 1 ml of isopropyl alcohol;

the sample was centrifuged at 14,000 G for 5 minutes and then the supernatant (containing the extracted lipids) was collected;

the supernatant was diluted 10 fold with isopropyl alcohol;

the diluted lipid extract was analyzed with a Direct Detect IR Spectrometer (Millipore), which provided the total lipid concentration of the supernatant (mg/ml);

the total lipids of the subcutis sample was quantified multiplying the supernatant lipid concentration (indention 4) by the preliminary dilution factor (indention 3) and then by the volume of isopropyl alcohol used for the lipid extraction (indention 1);

the residual pellet obtained from indention 2 was washed with 1 ml of isopropyl alcohol and, after another centrifugation this solvent was withdrawn;

the pellet was dried in a vacuum dry evaporator and then homogenized in 100 µl of proteolytic buffer (20 mM Tris HCl pH 7.5, 150 mM NaCl, 2 mM EDTA, 0.5% Triton X-100, 2 mM DTT, 1% protease inhibitor cocktail);

the extractive mixture was centrifuged at 14,000 G for 10 minutes and the supernatant was collected and analyzed with a Direct Detect IR Spectrometer (Millipore), which provided the total protein concentration of the supernatant (mg/ml);

the obtained total protein concentration was multiplied by the extractive volume (indention 7) in order to quantify the total proteins of the subcutis sample;

the total lipids (indention 5) were divided by the total proteins (indention 9) in order to obtain the amount of lipids per mg of proteins relative to the processed subcutis sample.

Table 15 shows the normalized total lipids (total lipids/total proteins) of the experimental groups, expressed as percentage ratio of the control group performance.

TABLE 15

Variation of normalized total lipids in human skin samples treated with ethanol extract (EtOH) and aqueous extract (Water) obtained from *Halimione*. The data are expressed as % ratio of the control group performance.

| Example | Sample | Amount | Average | Std. error | No. skin samples |
|---|---|---|---|---|---|
| 0 | Control | 0 | 100.0 | 13.6 | 4 |
| 68 | EtOH | 1.0 µg/ml | 143.5 | 16.4 | 4 |
| 69 | EtOH | 10 µg/ml | 107.9 | 27.0 | 4 |
| 70 | Water | 1.0 µg/ml | 119.5 | 21.8 | 4 |
| 71 | Water | 10 µg/ml | 125.8 | 26.6 | 4 |

The experimental results attest that both the extracts increased the amount of lipids in the skin subcutis. The more intense responses (+44%) was detected following the treatments with EtOH extract at 1.0 µg/ml, while the treatment at 10 µg/ml did not produced any relevant response. The water extract stimulated the lipogenesis at both the tested concentrations, inducing an increase of lipids comprised between 19 and 26%.

These data show that the extracts obtained from *Halimione* can significantly affect the metabolism of lipids and can be adopted for combating or preventing lipoatrophy of the skin.

Examples 72 to 75

Activity of Ethanolic and Aqueous Extracts Obtained from *Halimione* on the Lipid Metabolism of Full-Thickness Skin The previous experiment was repeated with skin-subcutis samples taken from another donor. The obtained results are showed in Table 16

TABLE 16

Variation of normalized total lipids in human skin samples treated with ethanol extract (EtOH) and aqueous extract (Water) obtained from *Halimione*. The data are expressed as % ratio of the control group performance.

| Example | Sample  | Amount      | Average | Std. error | No. skin samples |
|---------|---------|-------------|---------|------------|------------------|
| 0       | Control | 0           | 100.0   | 18.3       | 4                |
| 72      | EtOH    | 1.0 µg/ml   | 127.8   | 11.2       | 4                |
| 73      | EtOH    | 10 µg/ml    | 120.2   | 5.0        | 4                |
| 74      | Water   | 1.0 µg/ml   | 116.1   | 5.3        | 4                |
| 75      | Water   | 10 µg/ml    | 112.0   | 5.1        | 4                |

The subcutis samples treated with both the *Halimione* extracts showed an increased content in lipids, ranging from 12% to 29% higher than the control group. These data confirm that the tested extracts stimulate the adipose tissue lipogenesis and that they are suitable to be adopted for combating or preventing lipoatrophy of the skin.

Activity of *Halimione* Extracts on Human Sebaceous Glands

In order to evaluate the presence in *Halimione* of natural compounds active on sebogenesis, ex-vivo cultures of human sebaceous glands (hSGs) were set up and treated with different extracts obtained from this plant.

The responses of the treated hSGs, in comparison to the untreated group, were evaluated after 6 days of culture by analyzing their total lipid content and normalizing this value to the protein amount present in their composition, as already explained discussing the lipid quantification in subcutis.

Examples 76 to 80

Activity of Ethanolic and Aqueous Extracts Obtained from *Halimione* on the Lipid Metabolism of Human Sebaceous Glands (hSGs)

Two extracts were prepared from freshly harvested *Halimione* plants, as previously described, adopting ethanol and water as solvents. The extracts were prepared at concentrations varying between 8,000 and 11,600 µg/ml and each of these concentrated stocks was directly diluted in culture medium up to the final concentrations of 10, 1 and 0.1 µg/ml. The medium supplemented with ethanolic extract at 10 µg/ml also contained ethanol 0.125%, therefore the same amount of ethanol was added to the other culture media adopted in the experimental design (control and water extract).

Using micro-scissors and tweezers, hSGs were isolated from the pilosebaceous units of a scalp skin sample. They were seeded in 24-well plates at the density of 8 hSGs/well and then cultivated in 500 µl of modified William E medium. After 24 hours of culture, the viability of the hSGs was assessed by means of resazurine assay. Briefly, each hSGs group was transferred on a microplate well with 200 µl of 10% resazurin culture medium for 2 hours. During this period the resazurin, a non fluorescent blue dye, is reduced by living cells to the pink coloured and highly red fluorescent resorufin. At the end of the incubation, the medium was withdraw and analysed for the resazurin fluorescence in a plate reader (Em. 570 nm-Ex. 590 nm). The fluorescence signal positively correlates with the SG viability. Following the confirmation of the good viability of the cultured organs, the experimental treatments were started and continued up to day 6. The control received modified William E medium, while the samples submitted to experimental treatments received the same medium supplemented with the extracts. The culture medium was renewed every other day. After six days of organ culture, the viability of the hGSs was newly assessed via resazurine assay and then, attested their good condition, each group of hGSs was collected and analysed according the following protocol:

- Each hSG group was homogenized in 100 µl of isopropyl alcohol;
- The sample was centrifuged at 14,000 G for 5 minutes and then the supernatant (containing the extracted sebum) was collected;
- The sebum extract was analysed in triplicate with Direct Detect IR Spectrometer (Millipore), which provided the total lipid concentration of the supernatant (mg/ml);
- The total lipids of the hSGs was quantified multiplying the supernatant lipid concentration (indention 3) by the volume of isopropyl alcohol adopted for the lipid extraction (indention 1);
- The pellet remaining from indention 2 was dried by means of vacuum dry evaporator and then newly homogenized in 50 µl of proteolytic buffer (20 mM Tris/HCl pH 7.5, 150 mM NaCl, 2 mM EDTA, 0.5% Triton X-100, 2 mM DTT, 1% protease inhibitor cocktail);
- This extractive mixture was centrifuged at 14,000 G for 10 minutes and the supernatant was collected and analysed in triplicate with Direct Detect IR Spectrometer (Millipore);
- The obtained total protein concentration was multiplied by the extractive volume (indention 5) in order to quantify the total proteins of the hSGs;
- The total lipid amount (indention 4), i.e. the amount of sebum, was divided by the total proteins (indention 7) in order to obtain the normalized amount of lipids per mg of proteins (mg of lipids/mg of proteins).

The amounts of normalized total lipids obtained from the treated groups, i.e. the sebum produced by each group of hSGs, were expressed in percentage values respect to the value obtained in the control group and the results are shown in Table 17.

TABLE 17

Variation of sebum in hSGs treated with ethanol extract (EtOH) and aqueous extract (Water) obtained from *Halimione*. The data are expressed as % ratio of the control group performance. The values reported are mean values of three replicas of estimation of the lipid and protein amounts (see methodology above reported).

| Example | Sample  | Amount      | Average | Std. error |
|---------|---------|-------------|---------|------------|
| 0       | Control | 0           | 100.0   | 3.5        |
| 76      | EtOH    | 0.1 µg/ml   | 100.7   | 4.3        |
| 77      | EtOH    | 1.0 µg/ml   | 92.8    | 5.2        |
| 78      | EtOH    | 10 µg/ml    | 90.7    | 4.4        |
| 79      | Water   | 1.0 µg/ml   | 60.8    | 3.7        |
| 80      | Water   | 10 µg/ml    | 86.6    | 2.6        |

The results attest that the ethanolic extract inhibited the production between 7 and 9% following treatments respectively at 1 µg/ml and 10 µg/ml.

Furthermore, the aqueous extract induced a very intense inhibition of the sebum production, varying between 13 and 39% depending on the concentration of treatment. These data show that *Halimione* syntesizes compounds suitable to be exploited as seboregulators and these compounds are preferentially soluble in water.

Examples 81 to 86

Activity of Ethanolic and Aqueous Extracts Obtained from *Halimione* on the Lipid Metabolism of *Human sebaceous* Glands (hSGs)

In a new experiment, an ethanolic extract obtained from plants harvested in spring was tested in comparison with another one obtained from plants harvested in autumn. In the same experimental plan was included also the water extract already tested in the previous experiment, obtained from plants harvested in spring.

The experimental protocol was the same of the previous experiment. The obtained results are reported in Table 18.

TABLE 18

Variation of sebum in hSGs treated with ethanol extract (EtOH) obtained from plant harvested respectively in spring and autumn, and with aqueous extract (Water) obtained from *Halimione*. The data are expressed as % ratio of the control group performance. The values reported are mean values of three replicas of estimation of the lipid and protein amounts.

| Example | Sample | Amount | Average | Std. error |
|---|---|---|---|---|
| 0 | Control | 0 | 100.0 | 3.6 |
| 81 | EtOH spring | 1.0 µg/ml | 66.8 | 1.5 |
| 82 | EtOH spring | 10 µg/ml | 82.7 | 1.8 |
| 83 | EtOH autumn | 1.0 µg/ml | 94.1 | 1.2 |
| 84 | EtOH autumn | 10 µg/ml | 70.4 | 1.9 |
| 85 | Water | 1.0 µg/ml | 91.0 | 3.1 |
| 86 | Water | 10 µg/ml | 70.4 | 1.0 |

The data confirm the biological activity already disclosed in the previous experiment. The etanolic extracts inhibited the sebum production from 6 to 33%; both the spring and the autumnal extracts inhibited the sebogenesis about 30% following treatment with at least one of the two tested concentrations. This attests that the active principles included in the ethanolic extract are stably synthesized by *Halimione* throughout all the yearly cicle. The aqueous extract also inhibited sebogenesis 30%, confirming its intense activity on the hSGs.

Examples 87 to 89

Activity of Ethanolic and Aqueous Extracts Obtained from *Halimione* on the Lipid Metabolism of *Human sebaceous* Glands (hSGs)

A third experiment was performed in order to confirm the seboregulatory activity of the ethanolic and aqueous extracts of *Halimione*. The experimental protocol was the same described for the examples 76-80, but in this case just two concentrations of EtOH extract and one concentration of water extract were tested. The results are reported in Table 19.

TABLE 19

Variation of sebum in hSGs treated with ethanol extract (EtOH) and aqueous extract (Water) obtained from *Halimione*. The data are expressed as % ratio of the control group performance. The values reported are mean values of three replicas of estimation of the lipid and protein amounts.

| Example | Sample | Amount | Average | Std. error |
|---|---|---|---|---|
| 0 | Control | 0 | 100.0 | 2.7 |
| 87 | EtOH | 1.0 µg/ml | 81.3 | 1.4 |
| 88 | EtOH | 10 µg/ml | 79.1 | 2.1 |
| 89 | Water | 10 µg/ml | 76.1 | 2.3 |

All the treatments induced a significant inhibition of the sebum production, varying between 19 and 24%, confirming the biological activity already disclosed by the previous experiments.

What is claimed is:

1. A non-pharmaceutical method comprising topically administering an effective amount of an extract of *Halimione* sp. to skin or scalp of a subject suffering from hair loss and/or whitening or in need of promoting hair follicle growth and/or pigmentation, for modulating
   (i) keratinocyte differentiation in human hair, and/or
   (ii) melamin synthesis in human hair follicles, and/or
   (iii) hair growth by improving general wellness of the organ and/or by delaying the catagen in the human hair follicles.

2. The method of claim 1, comprising the additional step of obtaining the extract of *Halimione* sp. by treating the plant with a solvent selected from the group consisting of $C_1$-$C_4$ aliphatic alcohols, ethyl acetate, water and mixtures thereof, removing the dissolved extracts from the residues and recovering the pure extracts from the solvent.

3. The method of claim 2, comprising the following steps:
   (a) bringing the plant material, optionally minced or crushed or micronized, in contact with a solvent selected from the group consisting of $C_1$-$C_4$ aliphatic alcohols, ethyl acetate, water and mixtures thereof in an amount suitable for the active ingredients to move into the solvent phase, optionally at elevated temperatures,
   (b) removing the dissolved extract from the residue, and
   (c) recovering the pure extract from the solvent.

4. The method of claim 1, comprising topically administering the extract of *Halimione* sp. together with a cosmetically acceptable carrier selected from the group consisting of $C_1$-$C_4$ aliphatic alcohols, polyols having 3 to 12 carbon atoms, oil components, water and mixtures thereof.

5. The method of claim 1, wherein the extract is administered in an amount of from about 0.001 to about 35% b.w.—calculated on the final composition.

6. The method of claim 5, comprising administering the extract in an amount of about 0.01 to about 10% by weight.

7. The method of claim 6, comprising administering the extract in an amount of about 0.1 to about 3% by weight.

* * * * *